US007018827B1

(12) United States Patent
Zancope-Oliveira et al.

(10) Patent No.: US 7,018,827 B1
(45) Date of Patent: Mar. 28, 2006

(54) **NUCLEIC ACIDS OF THE M ANTIGEN GENE OF *HISTOPLASMA CAPSULATUM*, ANTIGENS, VACCINES AND ANTIBODIES, METHODS AND KITS FOR DETECTING HISTOPLASMAS**

(75) Inventors: Rosely M. Zancope-Oliveira, Rio de Janeiro (BR); Timothy J. Lott, Atlanta, GA (US); Leonard W. Mayer, Decatur, GA (US); Errol Reiss, Chamblee, GA (US); George S. Deepe, Terrace Park, OH (US)

(73) Assignees: The United States of America as represented by the Department of Health and Human Services, Washington, DC (US); University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/674,195

(22) PCT Filed: Apr. 27, 1999

(86) PCT No.: PCT/US99/09151

§ 371 (c)(1),
(2), (4) Date: Aug. 3, 2001

(87) PCT Pub. No.: WO99/55874

PCT Pub. Date: Nov. 4, 1999

Related U.S. Application Data

(60) Provisional application No. 60/083,676, filed on Apr. 30, 1998.

(51) Int. Cl.
*C12N 1/20* (2006.01)
*C12N 15/00* (2006.01)
*C07H 21/02* (2006.01)
*C07H 21/04* (2006.01)

(52) U.S. Cl. .............................. 435/252.3; 435/320.1; 536/23.1; 536/23.74

(58) Field of Classification Search ............. 435/252.3, 435/320.1; 536/23.1, 23.74
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,704,362 A | 11/1987 | Itakura et al. | |
| 4,965,188 A | 10/1990 | Mullis et al. | |
| 5,310,652 A | 5/1994 | Gelfand et al. | |
| 5,322,770 A | 6/1994 | Gelfand | |
| 5,352,579 A | 10/1994 | Milliman | |
| 5,545,522 A | 8/1996 | Van Gelder et al. | |
| 5,578,467 A | 11/1996 | Schuster et al. | |
| 5,624,833 A | 4/1997 | Gelfand et al. | |
| 5,693,501 A | * | 12/1997 | Lee et al. |

FOREIGN PATENT DOCUMENTS

WO    WO 99/55874    11/1999

OTHER PUBLICATIONS

Stryer (Biochemistry 3$^{rd}$ ed. New York, p 72), 1988.*
EMBL Database, Heidelberg, FRG Accession No. AF026268, Nov. 14, 1997, Zancope-Oliveira (created Nov. 14, 1997, updated Mar. 31, 1999).
Zancopé-Oliveira et al. "Molecular Cloning, Characterization, and Expression of the M Antigen of *Histoplasma capsulatum*" *Infect. Immun.* 67(4):1947-1953 (Apr., 1999).
Zancopé-Oliveira et al. "Isolation and Characterization of the M antigen of *Histoplasma capsulatum*" *Abstracts of the 97th General Meeting of the American Society for Microbiology* p. 266, F-35, (May, 1997).
Klimas "Delayed Hypersensitivity Skin Testing" *Manual of Clinical Laboratory Immunology* (5th ed.). eds. *Am. Soc. Microbio.* pp. 276-280 (1996).
Deepe et al. "Immunobiological Activity of Recombinant H Antigen From *Histoplasma capsulatum*" *Infect. Immun.* 63(8):3151-3157 (1995).
Zancopé-Oliveira et al. "Effects of Histoplasmin M Antigen Chemical and Enzymatic Deglycosylation on Cross-Reactivity in the Enzyme-Linked Immunoelectrotransfer Blot Method" *Clin. Diagn. Lab. Immunol.* 1(4):390-393 (Jul., 1994).
Zancopé-Oliveira et al. "Immunochemical Analysis of the H and M Glycoproteins from *Histoplasma capsulatum*" *Clin. Diagn. Lab. Immunol.* 1(5):563-568 (Sep., 1994).

(Continued)

Primary Examiner—Mark Navarro
(74) Attorney, Agent, or Firm—Needle & Rosenberg, PC

(57) ABSTRACT

The present invention provides the nucleotide sequence of the M antigen gene of *H. capsulatum*, which is set forth in the Sequence Listing as SEQ ID NO:1, a nucleic acid having the nucleotide sequence complementary thereto, and nucleic acids having a nucleotide sequence which is substantially the same as the foregoing nucleotide sequences. The present invention also provides vectors and host expressions systems containing the foregoing nucleic acids, and isolated or recombinantly-produced antigens encoded by the foregoing nucleic acids. The present invention further provides antibodies generated against the foregoing antigens, and methods and kits for detecting a previous or current *Histoplasma capsulatum* infection in a subject, and for diagnosing histoplasmosis.

15 Claims, No Drawings

OTHER PUBLICATIONS

Wheat "Diagnosis and Management of Histoplasmosis" *Eur. J. Clin. Microbiol. Infect. Dis.* 8(9):480-490 (May, 1989).

Keath et al., "Molecular cloning and sequence analysis of yps-3, a yeast-phase-specific gene in the dimorphic fungal pathogen *Histoplasma capsulatum*" *Microbiology* 140: 759-767 (1994).

Rossolini et al. "Use of deoxyinosine-containing primers vs. degenerate primers for polymerase chain traction based on ambiguous sequence information" *Mol. Cell. Probes* 8:91-98 (1994).
Zancopé-Oliveira et al. "Evaluation of cation exchange chromatography for the isolation of M glycoprotein from histoplasmin" *J. Med. and Vet. Mycology* 31:29-41 (1993).
Kaufman "Laboratory Methods for the Diagnosis and Confirmation of Systemic Mycoses" *Clin. Infect. Dis.* 14 (suppl.1):S23-S29 (1992).
Rotbart "Enzymatic RNA Amplification of the Enteroviruses" *J. Clin. Microbiol.* 28(3):438-442 (Mar., 1990).
Kawasaki "Amplification of RNA," pp. 21-27 in *PCR Protocols: A Guide to Methods and Applications*. eds. Innis et al., *Academic Press*, New York (1990).
Harris et al., "Characterization of Antigenic Determinants in Histoplasmin That Stimulate *Histoplasma capsulatum*-Reactive T Cells in Vitro" *Infect. Immun.* 56(9):2343-2349 (Sep., 1988).
Reiss et al. "Monoclonal Antibodies against the M-protein and Carbohydrate Antigens of Histoplasmin Characterized by the Enzyme-Linked Immunoelectrotransfer Blot Method" Infect. Immun. 53(3):540-546 (Sep., 1986).
Green et al. "Preparation of h and m Antigens of *Histoplasma capsulatum* Free of Heterologous Antigens" *Curr. Microbiol.* 12:209-216 (1985).
Kumar et al. "Cross-Reacting Human and Rabbit Antibodies to Antigens of *Histoplasma capsulatum, Candida albicans* and *Saccharomyces cerevisiae" Infect. Immun.* 48(3):806-812 (Jun. 1985).
Brake et al. "α-factor-directed synthesis and secretion of mature foreign proteins in *Saccharomyces cerevisiae" Proc. Nat. Acad. Sci.* USA 81:4642-4646 (Aug., 1984).
Sprouse "Determination of Molecular Weight. Isoelectric Point. and Glycoprotein Moiety for the Principal Skin Test-Reactive Component of Histoplasmin" *Infect. Immun.* 15 (1):263-271 (Jan., 1977).
Pine "Histoplasma Antigens: Their Production, Purification and Uses" *Contrib. Microbiol. Immunol.* 3:138-168 (1977).
Pine et al. "Procedures for the Production and Separation of H and M Antigens in Histoplasmin: Chemical and Serological Properties of the Isolated Products" *Mycopathologia* 61(3):131-141 (1977).
Green et al. "H and M Antigens of *Histoplasma capsulatum*: Preparation of Antisera and Location of These Antigens in Yeast-Phase Cells" *Infect. Immun.* 14(3):826-831 (Sep., 1976).
Bradley et al. "Purification, Composition, and Serological Characterization of Histoplasmin-H and M Antigens" *Infect. Immun.* 9(3):870-880 (May 1974).

* cited by examiner

SEQUENCE LISTING

```
<160> NUMBER OF SEQ ID NOS: 20

<210> SEQ ID NO 1
<211> LENGTH: 3862
<212> TYPE: DNA
<213> ORGANISM: Histoplasma capsulatum
<220> FEATURE:
<221> NAME/KEY: misc_feature
<222> LOCATION: 3258
<223> OTHER INFORMATION: n = g, a, c or t(u)

<400> SEQUENCE: 1
```

-continued

```
ggatcctgct ggctccgata actttgcttt atccaagggt ctcggcgaat gccaggtgcc      60
atcgatctat attttgaagt ttatcacctc aatggcttca ccccatgacg caccttttat     120
ttttattttc attcatcttc tctgtggcaa acatgcaggt atgcgagctc tggaccctgg     180
ggtgtggccc ttgatgcata tggtttattt atagccgccc ggaagccctg cctgttaaa     240
ttttggacct cctcccgcca ttctttccaa acttcgtgcg tccgtttccc atttcccccc     300
tccccatttg ggttccctat aggccactgc gtgctccact caagaagggt cccagtcaat     360
ttggtcccta ccctctccaa cactatctgc atatgtaata tatatcgata tctaactgcc     420
attgattatt tgtcttcttc agcatctttt tgtctcgagc aagcttactc cacgttcaat     480
tcaggggta aaaatgcggt cgctcaagct tatactcgcc tcggcgggtg ttgtttctgc      540
agcctgtccc tacatgtcag gggagatgcc tagcggtcag aaaggccccc tcgatcgccg     600
ccatgacact ctctccgacc ctacggacca gtttcttagc aagttttaca ttgacgatga     660
acagtcggtg ctaacaacgg acgtgggtgg tcccatcgag gaccaacaca gcctgaaggc     720
tggaaataga ggcccaactc tacttgagga ttttatcttc cgccagaaga ttcaacactt     780
tgatcatgag agggtatgta gatacaaaat atgtgaccgt gttgcaaatc cgctaattca     840
attttacgca ggttcctgag cgcgccgtcc atgctcgagg agctggtgcc catggcgtat     900
tcacatccta taataactgg tcgaatatca cagccgcatc cttcttgaac gcggcaggaa     960
agcagacacc agtattcgtg cggttttcta cagtcgctgg tagcagaggc agtgttgact    1020
ctgctcgcga tatccacgga tttgcgaccc gtctgtatac cgatgaaggc aattttggta    1080
agcattatat cgtggtagtc atactcataa cagcacaaca aatatgaata caaacccagg    1140
acctaggctg actactcggc aatgtagata tcgtcggaaa caacgttcca gtcttcttca    1200
ttcaggacgc tattcaattc cctgatttga ttcacgctgt caagccgcaa ccagacagtg    1260
aaattccca ggctgcaact gcacatgata cggcatggga tttcctcagc cagcagccca    1320
gctcattgca tgccctcttc tgggcaatgt caggacatgg aatccctcgc tcaatgcgtc    1380
atgttgatgg gtggggcgtc cataccttcc gacttgtcac cgacgagggc aactcgacct    1440
tggtcaagtt tcgctggaag accctccaag gaagagcggg cctggtatgg aagaggcac    1500
aggctcttgg cggaaagaat cccgacttcc atcgacaaga cctctgggat gccattgaat    1560
ctggaaggta ccctgagtgg gaggtaagat atgattcccc caaatcatta gttctgacag    1620
tgtttctctg ctctgtcggt tgctcttttc gtcttttttct atatcttcaa ctaagactga    1680
ctttatatac gttttactca tatagctggg cttttcaattg gtgaatgaag cagatcaatc    1740
caagtttgat ttcgatctat tagatcccac caaaatcatc ccagaagaac ttgttccttt    1800
caccccaatc ggaaaaatgg tcttgaaccg aaacccaaaa agttattttg ccgaaactga    1860
gcagatcatg gttggtccac cccctatata tttggaatat gaatacatgt atagctagat    1920
gaagcgtata tctaaatata tttccacagt tccaaccagg tcatgtagtt cgcggaatcg    1980
atttcacgga tgaccttttg cttcagggcc gcttgtactc ctaccttgac actcaattga    2040
atcgccatgg aggtcccaac ttcgagcaac tgccgatcaa cagaccccgc atcccattcc    2100
ataacaacaa tcgcgacggt gctggtaagc tacttctcac ctaccatgtc aacttccatc    2160
ttgacccaat cgatttgtat agagtattaa catccccgtc tgcacaggac aaatgttcat    2220
ccctctaaac acggccgcat atacacccaa ctcaatgagc aacggattcc cacaacaagc    2280
caaccggacc cataacagag gattcttcac cgcacctggg cgtatggtaa atggaccact    2340
```

-continued

```
agtgcgcgag ctcagcccga gcttcaacga cgtctggtcc caaccgcgtc tcttctacaa    2400
ctcactcacg gtcttcgaga agcaattcct cgtcaacgcc atgcgcttcg aaaactccca    2460
cgtgcggagt gaaaccgtgc gtaagaacgt catcatccag ctgaaccgcg tcgacaacga    2520
cctcgcccgc cgcgtcgcgc tagctatcgg cgtcgaaccc ccatcccgg acccaacctt    2580 ctaccacaac aaggcaaccg tccccatcgg caccttcggc acgaatctcc tgcggctcga    2640
cgggctgaaa atcgccctcc tgacaagaga cgacggtagc ttcacgatcg cggagcagct    2700
ccgggccgcg tttaacagcg ccaacaacaa agtagatatc gtcctagtgg gctcatcgct    2760
tgatccccaa cgcggcgtga acatgaccta ttccggcgcc gacggctcga tcttcgatgc    2820
cgtgatcgtc gtcggcggcc tgctcacgag cgcctcaacg caatacccaa gaggtcgccc    2880
gctcaggatt attacggatg catacgcgta tggaaagccc gttggcgccg tcggtgacgg    2940
tagcaatgaa gcccttcgtg acgtccttat ggccgctggt ggggatgcgt cgaatgggct    3000
ggaccagccc ggtgtgtata tttccaacga tgtgagtgag gcctacgtta gaagtgtctt    3060
ggacggattg acggcatatc ggttcttgaa tcggttcccg ttggatagaa gcttggtatg    3120
aggtttgggg cgcaaatatg ggtttactac cccccccccc ccctttttt ttttcctttt    3180 ctgtttttcc atctttggtt gaggtaatat tgcagatatc agtaaattgc gtttacgaaa    3240
gccggtgtca agcttcanga ggcctaatta atttgaagag gaggttgaag tgaaatcttg    3300
gtgtaactat aataatttat aataactaat aacttataat taatgtctat tgtaatttcc    3360
tctcacattc aatctatatt tgatccttgt cctttgtagc tgtttaaata taagccaaga    3420
gagacaaata atgatagatt aacaaataat tgcacaccca ataggccttc cctcacgata    3480
tcagatatta tctatcatgt tgtaatgata cctcaaaaat gccacaagct tgcctgatat    3540
tgaatattta tatgctgtaa atgtagggaa gagcgtacca tccaaataac cagaaaaaca    3600
tgttttagct taaatctca ctaaggtcgg tcgtgtctat ttgaaatggc tgcggcaagc    3660
tgactatctg ataaaaatgt ctgtatttcc gcttcacgac gcatgttatg actttcgaat    3720
atagataaaa cctgaacgat ttagcccctg ttgggggaaa taggggttag ggggcgagc    3780 tacatatcat tcccatatga ccaaaaacta aatagagat atatatatat atatatatat    3840
acaacacctt caaaaaggat cc                                            3862
```

<210> SEQ ID NO 2
<211> LENGTH: 707
<212> TYPE: PRT
<213> ORGANISM: Histoplasma capsulatum

<400> SEQUENCE: 2

```
Met Pro Ser Gly Gln Lys Gly Pro Leu Asp Arg Arg His Asp Thr Leu
 1               5                  10                  15

Ser Asp Pro Thr Asp Gln Phe Leu Ser Lys Phe Tyr Ile Asp Asp Glu
             20                  25                  30

Gln Ser Val Leu Thr Thr Asp Val Gly Gly Pro Ile Glu Asp Gln His
         35                  40                  45

Ser Leu Lys Ala Gly Asn Arg Gly Pro Thr Leu Leu Glu Asp Phe Ile
     50                  55                  60

Phe Arg Gln Lys Ile Gln His Phe Asp His Glu Arg Val Pro Glu Arg
 65                  70                  75                  80

Ala Val His Ala Arg Gly Ala Gly Ala His Gly Val Phe Thr Ser Tyr
                 85                  90                  95

Asn Asn Trp Ser Asn Ile Thr Ala Ala Ser Phe Leu Asn Ala Ala Gly
```

-continued

```
                100                 105                 110
Lys Gln Thr Pro Val Phe Val Arg Phe Ser Thr Val Ala Gly Ser Arg
            115                 120                 125
Gly Ser Val Asp Ser Ala Arg Asp Ile His Gly Phe Ala Thr Arg Leu
        130                 135                 140
Tyr Thr Asp Glu Gly Asn Phe Asp Ile Val Gly Asn Val Pro Val
145                 150                 155                 160
Phe Phe Ile Gln Asp Ala Ile Gln Phe Pro Asp Leu Ile His Ala Val
                165                 170                 175
Lys Pro Gln Pro Asp Ser Glu Ile Pro Gln Ala Ala Thr Ala His Asp
            180                 185                 190
Thr Ala Trp Asp Phe Leu Ser Gln Gln Pro Ser Ser Leu His Ala Leu
            195                 200                 205
Phe Trp Ala Met Ser Gly His Gly Ile Pro Arg Ser Met Arg His Val
        210                 215                 220
Asp Gly Trp Gly Val His Thr Phe Arg Leu Val Thr Asp Glu Gly Asn
225                 230                 235                 240
Ser Thr Leu Val Lys Phe Arg Trp Lys Thr Leu Gln Gly Arg Ala Gly
                245                 250                 255
Leu Val Trp Glu Glu Ala Gln Ala Leu Gly Gly Lys Asn Pro Asp Phe
            260                 265                 270
His Arg Gln Asp Leu Trp Asp Ala Ile Glu Ser Gly Arg Tyr Pro Glu
            275                 280                 285
Trp Glu Leu Gly Phe Gln Leu Val Asn Glu Ala Asp Gln Ser Lys Phe
        290                 295                 300
Asp Phe Asp Leu Leu Asp Pro Thr Lys Ile Ile Pro Glu Glu Leu Val
305                 310                 315                 320
Pro Phe Thr Pro Ile Gly Lys Met Val Leu Asn Arg Asn Pro Lys Ser
                325                 330                 335
Tyr Phe Ala Glu Thr Glu Gln Ile Met Phe Gln Pro Gly His Val Val
            340                 345                 350
Arg Gly Ile Asp Phe Thr Asp Asp Pro Leu Leu Gln Gly Arg Leu Tyr
            355                 360                 365
Ser Tyr Leu Asp Thr Gln Leu Asn Arg His Gly Gly Pro Asn Phe Glu
        370                 375                 380
Gln Leu Pro Ile Asn Arg Pro Arg Ile Pro Phe His Asn Asn Asn Arg
385                 390                 395                 400
Asp Gly Ala Gly Gln Met Phe Ile Pro Leu Asn Thr Ala Ala Tyr Thr
                405                 410                 415
Pro Asn Ser Met Ser Asn Gly Phe Pro Gln Gln Ala Asn Arg Thr His
            420                 425                 430
Asn Arg Gly Phe Phe Thr Ala Pro Gly Arg Met Val Asn Gly Pro Leu
            435                 440                 445
Val Arg Glu Leu Ser Pro Ser Phe Asn Asp Val Trp Ser Gln Pro Arg
        450                 455                 460
Leu Phe Tyr Asn Ser Leu Thr Val Phe Glu Lys Gln Phe Leu Val Asn
465                 470                 475                 480
Ala Met Arg Phe Glu Asn Ser His Val Arg Ser Glu Thr Val Arg Lys
                485                 490                 495
Asn Val Ile Ile Gln Leu Asn Arg Val Asp Asn Asp Leu Ala Arg Arg
            500                 505                 510
Val Ala Leu Ala Ile Gly Val Glu Pro Pro Ser Pro Asp Pro Thr Phe
            515                 520                 525
```

```
Tyr His Asn Lys Ala Thr Val Pro Ile Gly Thr Phe Gly Thr Asn Leu
    530                 535                 540

Leu Arg Leu Asp Gly Leu Lys Ile Ala Leu Leu Thr Arg Asp Asp Gly
545                 550                 555                 560

Ser Phe Thr Ile Ala Glu Gln Leu Arg Ala Ala Phe Asn Ser Ala Asn
                565                 570                 575

Asn Lys Val Asp Ile Val Leu Val Gly Ser Ser Leu Asp Pro Gln Arg
            580                 585                 590

Gly Val Asn Met Thr Tyr Ser Gly Ala Asp Gly Ser Ile Phe Asp Ala
        595                 600                 605

Val Ile Val Val Gly Gly Leu Leu Thr Ser Ala Ser Thr Gln Tyr Pro
    610                 615                 620

Arg Gly Arg Pro Leu Arg Ile Ile Thr Asp Ala Tyr Ala Tyr Gly Lys
625                 630                 635                 640

Pro Val Gly Ala Val Gly Asp Gly Ser Asn Glu Ala Leu Arg Asp Val
                645                 650                 655

Leu Met Ala Ala Gly Gly Asp Ala Ser Asn Gly Leu Asp Gln Pro Gly
            660                 665                 670

Val Tyr Ile Ser Asn Asp Val Ser Glu Ala Tyr Val Arg Ser Val Leu
        675                 680                 685

Asp Gly Leu Thr Ala Tyr Arg Phe Leu Asn Arg Phe Pro Leu Asp Arg
    690                 695                 700

Ser Leu Val
705

<210> SEQ ID NO 3
<211> LENGTH: 8
<212> TYPE: PRT
<213> ORGANISM: Histoplasma capsulatum

<400> SEQUENCE: 3

Ser Asp Pro Thr Asp Gln Phe Leu
 1               5

<210> SEQ ID NO 4
<211> LENGTH: 15
<212> TYPE: PRT
<213> ORGANISM: Histoplasma capsulatum

<400> SEQUENCE: 4

Asp Phe Ile Phe Arg Gln Lys Ile Gln His Phe Asp His Glu Arg
 1               5                  10                  15

<210> SEQ ID NO 5
<211> LENGTH: 9
<212> TYPE: PRT
<213> ORGANISM: Histoplasma capsulatum

<400> SEQUENCE: 5

Thr Leu Gln Gly Arg Ala Gly Leu Val
 1               5

<210> SEQ ID NO 6
<211> LENGTH: 16
<212> TYPE: PRT
<213> ORGANISM: Histoplasma capsulatum

<400> SEQUENCE: 6

Ala Gln Ala Leu Gly Gly Lys Asn Pro Asp Phe His Arg Gln Asp Leu
```

```
<210> SEQ ID NO 7
<211> LENGTH: 6
<212> TYPE: PRT
<213> ORGANISM: Histoplasma capsulatum

<400> SEQUENCE: 7

Ser Gly Arg Tyr Pro Glu
1               5

<210> SEQ ID NO 8
<211> LENGTH: 10
<212> TYPE: PRT
<213> ORGANISM: Histoplasma capsulatum

<400> SEQUENCE: 8

Phe Asp Phe Asp Leu Leu Asp Pro Thr Lys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence;
      M antigen-specific oligonucleotide

<400> SEQUENCE: 9

Ile Ile Pro Glu Glu Leu Val Pro Phe Thr Pro Ile Gly Lys
1               5                   10

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence; sense
      amplification primer
<220> FEATURE:
<221> NAME/KEY: misc_feature
<222> LOCATION: 3
<223> OTHER INFORMATION: r = a or g
<220> FEATURE:
<221> NAME/KEY: misc_feature
<222> LOCATION: 6, 12, 15
<223> OTHER INFORMATION: y = c or t
<220> FEATURE:
<221> NAME/KEY: misc_feature
<222> LOCATION: 9
<223> OTHER INFORMATION: v = g, c or a

<400> SEQUENCE: 10
aaraayccvg aytty                                           15

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence; anti-sense
      amplification primer
<220> FEATURE:
<221> NAME/KEY: misc_feature
<222> LOCATION: 3, 9
<223> OTHER INFORMATION: n = g, a, c or t(u)
<220> FEATURE:
<221> NAME/KEY: misc_feature
<222> LOCATION: 6
<223> OTHER INFORMATION: d = g, a or t(u)
```

```
<220> FEATURE:
<221> NAME/KEY: misc_feature
<222> LOCATION: 12
<223> OTHER INFORMATION: r = a or g

<400> SEQUENCE: 11
ttnccdatng traa                                                           14

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence; sense cDNA
      amplification primer

<400> SEQUENCE: 12
cggaatcctc cgaccctacg ga                                                  22

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence; anti-sense
      cDNA amplification primer

<400> SEQUENCE: 13
accaagcttc tatccaacgg gaaccga                                             27

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence/Note =
      Synthetic Construct
<220> FEATURE:
<221> NAME/KEY: misc_feature
<222> LOCATION: 1
<223> OTHER INFORMATION: d = g, a or t(u)

<400> SEQUENCE: 14
dcgaagtcga ggctttcagc atg                                                 23

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence/Note =
      Synthetic Construct
<220> FEATURE:
<221> NAME/KEY: misc_feature
<222> LOCATION: 1
<223> OTHER INFORMATION: d = g, a or t(u)

<400> SEQUENCE: 15
dtattagctc tagaattacc acgggtatcc aagtagtaag g                             41

<210> SEQ ID NO 16
<211> LENGTH: 41
<212> TYPE: DNA
<213> ORGANISM: Artificial Sequence
<220> FEATURE:
```

```
-continued

<223> OTHER INFORMATION: Description of Artificial Sequence/Note =
      Synthetic Construct
<220> FEATURE:
<221> NAME/KEY: misc_feature
<222> LOCATION: 1
<223> OTHER INFORMATION: d = g, a or t(u)

<400> SEQUENCE: 16
dccccgaagg gcattggttt tttatctaat aaatacaccc c                    41

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence/Note =
      Synthetic Construct
<220> FEATURE:
<221> NAME/KEY: misc_feature
<222> LOCATION: 1
<223> OTHER INFORMATION: d = g, a or t(u)

<400> SEQUENCE: 17
dcgaagtcga ggctttcagc atg                                        23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence/Note =
      Synthetic Construct

<400> SEQUENCE: 18
dcatgctgaa agcctcgact tcg                                        23

<210> SEQ ID NO 19
<211> LENGTH: 23
<212> TYPE: RNA
<213> ORGANISM: Artificial Sequence
<220> FEATURE:
<223> OTHER INFORMATION: Description of Artificial Sequence/Note =
      Synthetic Construct
<220> FEATURE:
<221> NAME/KEY: misc_feature
<222> LOCATION: 1
<223> OTHER INFORMATION: r = a or g

<400> SEQUENCE: 19
rcaugcugaa agccucgacu ucg                                        23

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence/Note =
      Synthetic Construct
<220> FEATURE:
<221> NAME/KEY: misc_feature
<222> LOCATION: 1
<223> OTHER INFORMATION: r = a or g

<400> SEQUENCE: 20
rcgaagucga ggcuuucagc aug                                        23
```

NUCLEIC ACIDS OF THE M ANTIGEN GENE OF *HISTOPLASMA CAPSULATUM*, ANTIGENS, VACCINES AND ANTIBODIES, METHODS AND KITS FOR DETECTING HISTOPLASMAS

CROSS REFERENCE TO RELATED APPLICATIONS

The present application claims priority to International Application No. PCT/US99/09151, filed on Apr. 27, 1999, which claims benefit of U.S. Provisional Patent Application Ser. No. 60/083,676, filed Apr. 30, 1998.

BACKGROUND OF THE INVENTION

1. Field of the Invention

The present invention relates to reagents and methods for the detection of histoplasmosis. In particular, the present invention relates to nucleic acids (DNAs) relating to the M antigen gene of *Histoplasma capsulatum*; to vectors and host expression systems containing these nucleic acids; to nucleic acids (RNAs) which encode the M antigen of *H. capsulatum*; to isolated and recombinantly-produced antigens encoded by these nucleic acids; to antibodies produced against these antigens; to methods and kits for detecting histoplasmosis using these nucleic acids, antigens and antibodies; and to vaccines for the treatment or prevention of histoplasmosis.

2. Background

Histoplasmosis is a systemic fungal disease resulting from the inhalation or, less frequently, the ingestion of spores of the fungus *Histoplasma capsulatum*, variety capsulatum, which is worldwide in distribution. The infection often causes acute pneumonia, or disseminated reticuloendothelial hyperplasia, or an influenza-like illness with joint effusion and erythema nodosum. Reactivated infection involves the lungs, meninges, heart, peritoneum and adrenals. Clinically inapparent or mild disease can result from limited, primary site infection of *H. capsulatum* in the lungs, but an often life-threatening, disseminated form of histoplasmosis can occur in immunodeficient patients, particularly the elderly, and those who have acquired immunodeficiency syndrome (AIDS). It is important to properly identify *H. capsulatum* from other fungal species in order to determine the proper treatment for a fungal infection.

*H. capsulatum* is a dangerous, dimorphic, pathogenic fungus which, under different environmental conditions, may exist as either the yeast or mold phase. The organism exists as a multicellular mycelium at room temperature in rich soils, and in organic matter, in temperate environments worldwide, and proliferates as a unicellular yeast form at 37° C., and in infected host tissues. Only the yeast phase is known to survive within tissues, or within macrophages. The unicellular yeast form reproduces by budding on specialized media at 37° C. The mold form produces multicellular filamentous colonies that consist of cylindrical tubular structures called hyphae, and may contain microconidia and macroconidia which primarily grow under appropriate soil conditions, or on specialized fungal media, at 25° C. *H. capsulatum* occurs throughout the world, particularly in Brazil, Africa, India, Southeast Asia and the United States, but is most commonly found in soil from the fertile river valleys (Mississippi and Missouri river valleys) of the central United States.

*H. capsulatum* is associated with bird (particularly black bird and seagull) and bat excrement. (See, for example, Loyd et al., *Histoplasma capsulatum*. In *Principles and Practice of Infectious Disease* (3rd ed., Coordinating ed., Mandell et al., New York, (1990)); Wheat, "Diagnosis and Management of Histoplasmosis," *Eur. J. Clin. Microbiol. Infect. Dis.* 8:480 (1989).) The fungus infects the soil, and the resulting infected soil is often used as a habitat by birds and/or bats.

In addition to *H. capsulatum* var. *capsulatum*, two variants of *Histoplasma* exist: *H. capsulatum* var. *duboisii* (African histoplasmosis) and *H. capsulatum* var. *farciminosum* (epizootic lymphangitis of horses and mules). (See, for example, Rippon, *Histoplasmosis*. In *Medical Mycology The Pathogenic Fungi and the Pathogenic Actinomycets* (3rd ed., Saunders Company, Chapter 15 (1988)).) Many strains of *H. capsulatum* are currently deposited with the American Type Culture Collection (ATCC), 12301 Parklawn Drive, Rockville, Md., 20852. *H. capsulatum* strain CDC6623, deposited under accession number ATCC 26320, is discussed in Pine et al., "Procedures for the Production and Separation of H and M Antigens in Histoplasmin, and Chemical and Serological Properties of the Isolated Products," *Mycopathlogia* 61:131–141 (1977). The following other strains or variants of *H. capsulatum* are also deposited with the ATCC: *H. capsulatum* (attenuated Downs strain, filamentous phase, accession number ATCC 38904), *H. capsulatum* (attenuated Downs strain, yeast phase, accession number ATCC 38904), *H. capsulatum* (filamentous phase, accession number ATCC 11407), *H. capsulatum* (yeast phase, accession number ATCC 11407), *H capsulatum* variant *duboisii* (filamentous phase, accession number ATCC 32281), *H. capsulatum* variant duboisii (yeast phase, accession number ATCC 32281), *H. capsulatum* variant *farciminosum* (filamentous phase, accession number ATCC 58332) and *H. capsulatum* variant *farciminasum* (yeast phase, accession number ATCC 58332).

The M antigen of *H. capsulatum* is a pluripotent glycoprotein having a molecular mass of 94 kDa, an isoelectric point of 4.7, oligosaccharide side chains, glycosidic epitopes which are N-linked to the peptide core, and protein epitopes, which have been shown to be unique to the *H. capsulatum* fungus. The peptide epitopes react with human antibodies, are not affected by N-deglycosylation, and trigger the proliferation of T cells. The M antigen is an immunodominant antigen of *H. capsulatum*, and elicits both humoral and cell-mediated immune responses. The glycopeptide bonds present in the glycoprotein are N linked. The M antigen of *H. capsulatum* is considered to be the immunodominant antigen of *H. capsulatum* because antibodies generated against the M antigen are first to arise in infection, and are more commonly present during all phases of histoplasmosis. Because the presence of this M antigen is indicative of histoplasmosis infection, the M antigen can serve as a marker for histoplasmosis infection. However, the biological identity of the M antigen has remained unknown. One report demonstrated that M protein was a catalase, based upon its ability to react with anti-catalase antibodies.

Currently, histoplasmosis is diagnosed by culture, or by the demonstration of a rise in complement-fixing antibody titers in serum. A definitive diagnosis of an *H. capsulatum* infection currently requires the isolation and propagation of the fungus, which is time-consuming and lacking in sensitivity, and which is dangerous for laboratory personnel, who must take extreme caution to prevent inhalation of the pathogenic fungus, so as not to become ill with a pulmonary infection. Further, only small quantities of antigens of *H. capsulatum* for use as biological reagents may be prepared in this manner.

Conventional laboratory identification methods used to isolate and identify *H. capsulatum* include the culture of a clinical specimen at room temperature on specialized fungal media. This procedure isolates the slower growing *H. capsulatum* colonies from possible contaminants, such as bacteria, and from faster growing saprobic fungi. This method, however, has several disadvantages. Because the growth of *H. capsulatum* to a visible colony normally takes from about two to four weeks, and sometimes as long as 12 weeks, this procedure is very slow. (See, for example, Rippon, Histoplasmosis. In *Medical Mycology, The Pathogenic Fungi and the Pathogenic Actinomyestes*, supra.; Koneman at al., *Laboratory Identification of Molds*, in *Practical Laboratory Mycology*, (3rd ed. Williams & Wilkins (1985)); and McGinnis, *Histoplasma capsulatum*. In *Laboratory Handbook of Medical Mycology* (Academic Press (1986)).) Further, additional growth is required before the characteristic colony morphology and microscopic sporulation pattern with tuberculate macroconidia may be observed. In addition, approximately 10% of cultures produce only smooth-walled macroconidia, and some cultures fail to sporulate. Moreover, many species of fungi other than *H. capsulatum*, such as *Blastomyces dermatitidis, Chrysosporium* sp., and *Sepedonium* sp., produce similar colony and sporulation characteristics. Thus, additional testing is usually necessary to definitively identify the organism.

One method of converting the mycelial colony of *H. capsulatum* to the yeast phase is performed by subculturing the organism onto highly enriched cysteine-containing media, and incubating it at 35°–37° C. However, conversion to the yeast phase is often difficult, and may require several additional subcultures at three-day intervals.

Serologic evidence is the prime diagnostic indicator of histoplasmosis. Such evidence may be obtained with several serologic tests, such as the immunodiffusion test, which detects precipitants against the species-specific H and M antigens found in histoplasmin. (See, for example, Kaufman, "Laboratory Methods for the Diagnosis and Confirmation of Systemic Mycoses," *Clin. Infect. Dis.* 14:23–29 (1992), and Wheat, "Diagnosis and Management of Histoplasmosis," supra.)

Histoplasmin, an unpurified culture supernatant obtained from the mycelial phase of *H. capsulatum* grown in a chemically-defined medium containing *H. capsulatum* M antigens is currently used to probe both humoral and cell-mediated responses in patients with histoplasmosis. It is used for the serologic diagnosis of histoplasmosis, and as a skin test antigen to demonstrate delayed hypersensitivity to infection in skin tests for histoplasmosis. The purification of histoplasmin is described by Bradley et al, "Purification, Composition, and Serological Characterization of Histoplasmin-H and M Antigens," *Infect. Immun.* 9:870–880 (1974). The preparation of H and M antigens of *H. capsulatum* free of heterologous antigens is described by Green et al., "Preparation of h and m Antigens of *Histoplasma capsulatum* Free of Heterologous Antigens," *Curr. Microbiol.* 12:209–216 (1985). (See also, Pine, "Histoplasma antigens: their Production, Purification and Uses," *Contrib. Microbiol. Immunol.* 3:138–168 (1977).) The preparation of antisera to the M antigen is described by Green et al., "H and M Antigens of *Histoplasma capsulatum*: Preparation of Antisera and Location of these Antigens in Yeast-Phase Cells," *Infect. Immun.* 14:826–831 (1976). General information concerning the serodiagnosis of fungal diseases is present in L. Kaufman et al., *Serodiagnosis of Fungal Diseases*, in *Manual of Clinical Laboratory Immunology* (3rd ed., American Society for Microbiology, Washington, D.C. (1988)).

Although the M antigen of *H. capsulatum* is useful in immunoassays for the diagnosis of histoplasmosis, purification of the M antigen from a batch culture is a laborious and low-yield process. The use of a recombinantly-produced M antigen of *H. capsulatum* in such immunoassays would significantly diminish the labor necessary to obtain M antigens which are pure enough to be useful in the immunoassays, and would result in high yields of the M antigen.

A need presently exists for biological reagents which can be produced and purified quickly and safely, and in large quantities, and which can be used in diagnostic assays to rapidly, easily and accurately detect a previous or current infection by *H. capsulatum*, and to diagnose histoplasmosis. A need also presently exists for a method of rapidly, easily and accurately detecting a previous or current infection by *H. capsulatum*, and to diagnose histoplasmosis. Such biological reagents and methods would allow a clinician to improve the speed and accuracy of processing large numbers of clinical samples. Such reagents and methods would also aid the clinician in patient management, eliminate unnecessary tests, improve the speed, ease and accuracy of diagnosis and prognosis, help control histoplasmosis infection and reduce the use of unnecessary medications.

Accordingly, the present invention provides the DNA nucleotide sequence of the M antigen gene of *H. capsulatum*, and of related nucleotide sequences, which can be used to safely and rapidly produce, by recombinant DNA techniques, large quantities of the M antigen of *H. capsulatum* when inserted into a vector and placed into a suitable host for protein expression. The recombinantly-produced M antigens may be quickly and safely produced in large quantities in a pure, undegraded form. The present invention also provides the RNA nucleotide sequence which encodes the M antigen of *H. capsulatum*, and related nucleotide sequences. Nucleic acids, and fragments thereof, within the invention can also be used as nucleic acid probes in hybridization assays, or as primers in polymerase chain reaction assays, to detect *H. capsulatum* in clinical samples.

The present invention also provides the deduced amino acid sequence of the *H. capsulatum* M antigen. Isolated and recombinant M antigens encoded by nucleic acids within the present invention can be used as biological reagents in a wide variety of tests for histoplasmosis, such as skin tests, and immunoassays to detect a previous or current *H. capsulatum* infection in a tissue or fluid sample obtained from a human being or animal suspected of having, or having had, histoplasmosis. For example, these antigens can be used as skin test antigens to ascertain the cell-mediated immune status of persons who have been exposed to *H. capsulatum*. The nucleic acids and antigens of the invention can also be used in a vaccine for the prevention or treatment of histoplasmosis.

The present invention also provides antibodies generated against the above antigens, which can be used in a wide variety of immunoassays to detect a current infection by *H. capsulatum*.

The present invention further provides methods for the detection of histoplasmosis, and related kits, using nucleic acids, antigens or antibodies within the invention.

The nucleic acids, vectors, hosts, isolated and recombinantly-produced antigens, antibodies, methods of detection and kits of the present invention permit the safe, direct, rapid, efficient, and accurate detection of a previous or current infection by *H. capsulatum* in a patient, and a positive diagnosis of histoplasmosis.

This patent application is believed to be the first report of the nucleotide sequence of the *H. capsulatum* M antigen gene, the nucleotide sequence which encodes the *H. capsulatum* M antigen, and of the amino acid sequence of the *H. capsulatum* M antigen.

3. Description of the Related Art

Zancopé-Oliveira et al., "Immunochemical Analysis of the H and M Glycoproteins from *Histoplasma Capsulatum*," *Clin. Diagn. Lab. Immunol. Vol.* 1, No. 5, 563–568 (1994), describes the use of different physicochemical methods to characterize the M and H antigens obtained from histoplasmin.

Zancopé-Oliveira et al., "Evaluation of Cation Exchange Chromatography for the Isolation of M Glycoprotein from Histoplasmin," *Journal of Medical and Veterinary Mycology* 31, 29–41 (1993), describes the development of chromatography procedures to isolate the M antigen from histoplasmin, and the monitoring of the physical, chemical and serological properties of the protein.

Zancopé-Oliveira et al., "Effects of Histoplasmin M. Antigen Chemical and Enzymatic Declycosylation on Cross-Reactivity in the Enzyme-Linked Immunoelectrotransfer Blot Method," *Clinical and Diagnostic Laboratory Immunology* 1, No. 4, 390–393 (1994), describes an evaluation of the enzyme-linked immunoelectrotransfer blot (EITB) method as a suitable method for detecting antibodies present in sera from patients with histoplasmosis against M antigen, and the effect of chemical and enzymatic deglysolyation of M antigen as a means of increasing diagnostic specificity. The assay described in this article was stated to demonstrate 100% sensitivity with histoplasmosis serum samples, all of which were stated to react with the *H. capsulatum* M antigen.

Green et al. "Preparation of h and m Antigens of *Histoplasma capsulatum* Free of Heterologous Antigens," supra., describe the use of a salt gradient elution of crude histoplasmin on CM-sepharose CL6B at pH 3.0 in a one-step procedure to isolate the H, M and non-M antigens of *H. capsulatum*, and free them of any C antigen common to other pathogenic fungi to produce highly-purified antigens for use in immunoassays. This reference provides (Table 4 on Page 213) the gross amino acid composition (mole percent of sixteen amino acids) of the *H. capsulatum* M antigen, but not the amino acid sequence thereof.

Keath, "Molecular Cloning and Sequence Analysis of yps-3, a Yeast-Phase-Specific Gene in the Dimorphic Fungal Pathogen *Histoplasma capsulatum*," *Microbiology* 140, 759–767 (1994), describes the cloning of the *H. capsulatum* yeast-phase-specific (yps-3) gene to clarify the mechanisms underlying pathogenesis and morphogenesis in the fungus *H. capsulatum*. The nucleotide sequence of the yps-3 gene, and the predicted amino acid sequence of its product, are provided.

Deepe et al., "Immunobiological Activity of Recombinant H Antigen From *Histoplasma capsulatum*," *Infection and Immunity*, Vol. 63, No. 8, 3151–3157 (1995), describe the isolation and sequencing of the H antigen gene of *H. capsulatum*, and the recombinant production of the *H. capsulatum* H antigen in the bacterial expression vector pET 19b.

U.S. Pat. No. 5,352,579 describes nucleic acid hybridization assay probes which are stated to be specific for *H. capsulatum* and no other fungi, and which have the nucleotide sequence 5 CGAAGTCGAGGCTTTCAGCATG3, or the nucleotide sequence complementary thereto. A probe having the above nucleotide sequence is stated to hybridize to the 18S rRNA of *H. capsulatum* corresponding to bases 172–193 of *Sacchromyces cerevisiae*. This patent also describes the use of helper probes having the sequence 5'TATTAGCTCTAGAATTACCACGGGTATC-CAAGTAGTAAGG3, or the sequence 5'CCCCGAAGGGCATTGGTTTTT-TATCTAATAAATACACCCC3'.

None of the above documents teaches or suggests the DNA nucleotide sequence of the *H. capsulatum* M antigen gene, the RNA nucleotide sequence which encodes the *H. capsulatum* M antigen, the amino acid sequence of the *H. capsulatum* M antigen, or the production of the *H. capsulatum* M antigen using recombinant DNA techniques.

SUMMARY OF THE INVENTION

The present invention provides the nucleotide sequence of the M antigen gene (DNA) of the *Histoplasma capsulatum* species of fungus, which is set forth in the Sequence Listing as SEQ ID NO:1.

The present invention also provides a nucleic acid specific to *Histoplasma capsulatum* comprising a nucleic acid having a nucleotide sequence as set forth in the Sequence Listing as SEQ ID NO:1, a nucleic acid having a nucleotide sequence which is complementary to the nucleotide sequence set forth in the Sequence Listing as SEQ ID NO:1, a nucleic acid which is substantially the same as a nucleic acid having a nucleotide sequence as set forth in the Sequence Listing as SEQ ID NO:1, a nucleic acid which is substantially the same as a nucleic acid having a nucleotide sequence which is complementary to the nucleotide sequence set forth in the Sequence Listing as SEQ ID NO:1, a fragment of a nucleic acid having a nucleotide sequence as set forth in the Sequence Listing as SEQ ID NO:1, a fragment of a nucleic acid having a nucleotide sequence which is complementary to the nucleotide sequence set forth in the Sequence Listing as SEQ ID NO:1, a fragment of a nucleic acid which is substantially the same as a nucleic acid having a nucleotide sequence as set forth in the Sequence Listing as SEQ ID NO:1, or a fragment of a nucleic acid having a nucleotide sequence which is substantially the same as a nucleic acid which is complementary to the nucleotide sequence set forth in the Sequence Listing as SEQ ID NO:1. The isolated nucleic acid of this invention does not contain the nucleotide sequence 5'CGAAGTC-GAGGCTTTCAGCATG3, the nucleotide sequence complementary thereto, the nucleotide sequence 5'TATT-AGCTCTAGAATTACCACGGGTATCCAAGTAGTAAGG3, the nucleotide sequence complementary thereto, the nucleotide sequence 5'CCCCGAAGGGCATTGGTTTTT-TATCTAATAAATACACCCC3, or the nucleotide sequence complementary thereto. Further, the isolated nucleic acid is not a nucleic acid consisting essentially of between 10 and 100 nucleotides which is able to form a hybrid at 60° C. with a nucleotide polymer having a nucleotide base sequence of 5 CGAAGTCGAGGCTTTCAGCATG3, 5 CATGCT-GAAAGCCTCGACTTCG3', CAUGCUGAAAGCCUC-GACUUCG3 or 5 CGAAGUCGAGGCUUUCAGCAUG3.

The present invention further provides the amino acid sequence of the isolated or recombinantly-produced M antigen of the *Histoplasma capsulatum* species of fungus, which is set forth in the Sequence Listing as SEQ ID NO:2. The antigen is encoded by a nucleic acid (RNA) having a nucleotide sequence which is complementary to the nucleotide sequence set forth in the Sequence Listing as SEQ ID NO:1.

The present invention also provides an isolated or recombinantly-produced antigen specific to Histoplasma capsulatum comprising a polypeptide encoded by a nucleic acid having a nucleotide sequence which is complementary to the nucleotide sequence set forth in the Sequence Listing as SEQ ID NO:1, a fragment of a polypeptide encoded by a nucleic acid having a nucleotide sequence which is complementary to the nucleotide sequence set forth in the Sequence Listing as SEQ ID NO:1, a polypeptide encoded by a nucleic acid which is substantially the same as a nucleic acid having a nucleotide sequence which is complementary to the nucleotide sequence set forth in the Sequence Listing as SEQ ID NO:1, or a fragment of a polypeptide encoded by a nucleic acid which is substantially the same as a nucleic acid having a nucleotide sequence which is complementary to the nucleotide sequence set forth in the Sequence Listing as SEQ ID NO:1.

The invention further provides monoclonal or polyclonal antibodies generated against one of the isolated or recombinantly-produced antigens described above.

The present invention also provides a vector comprising a nucleic acid specific to Histoplasma capsulatum, wherein the nucleic acid has a nucleotide sequence as set forth in the Sequence Listing as SEQ ID NO:1, has a nucleotide sequence which is substantially the same as a nucleic acid having a nucleotide sequence as set forth in the Sequence Listing as SEQ ID NO:1, is a fragment of a nucleic acid having a nucleotide sequence as set forth in the Sequence Listing as SEQ ID NO:1, or is a fragment of a nucleic acid which is substantially the same as a nucleic acid having a nucleotide sequence as set forth in the Sequence Listing as SEQ ID NO:1, and wherein the vector is suitable for expressing the nucleic acid.

The present invention still further provides a host for expressing an antigen which is specific to Histoplasma capsulatum comprising a vector containing a nucleic acid, wherein the vector is suitable for expressing the nucleic acid, and wherein the nucleic acid is as described above for the vector of the present invention.

The present invention also provides a vaccine for the treatment or prevention of histoplasmosis comprising:
 (a) a nucleic acid, or an isolated or recombinantly-produced antigen, which is specific to Histoplasma capsulatum; and (b) a pharmaceutically-acceptable carrier for the nucleic acid or antigen, wherein the nucleic acid in a nucleic acid as described above, and wherein the antigen is an antigen as described above.

The present invention further provides a method for detecting a previous or current Histoplasma capsulatum infection in a subject, comprising: (a) contacting a fluid or tissue sample from the subject which contains antibodies with an isolated or recombinantly-produced antigen which is specific to Histoplasma capsulatum; and (b) detecting the presence of binding between the antibodies and the antigen, the presence of binding indicating the presence of a previous or current Histoplasma capsulatum infection in a subject, wherein the antigen is one of the antigens described above.

The present invention further provides a method for detecting a past exposure to the fungus Histoplasma capsulatum comprising: (a) injecting intradermally in the skin of a subject a liquid containing an isolated or recombinantly-produced antigen which is specific to Histoplasma capsulatum; and (b) observing the skin of the subject at the injection site at one or more predetermined times after injection for the presence of swelling of the skin, the presence of swelling of the skin indicating a past exposure by the subject to the fungus Histoplasma capsulatum, wherein the antigen is one of the antigens described above.

The present invention still further provides a kit for detecting a previous or current Histoplasma capsulatum infection in a sample comprising: (a) a nucleic acid, an isolated or recombinantly-produced antigen, or an antibody described above; and (b) instructions describing the use of the nucleic acid, antigen or antibody in the detection of a previous or current Histoplasma capsulatum infection.

The present invention also provides a method for detecting a current H. capsulatum infection in a subject suspected of having an H. capsulatum infection comprising: (a) contacting a fluid or tissue sample from the subject which contains antigens with antibodies generated against an antigen which contains an epitope which is unique to H. capsulatum; and (b) detecting the presence of binding between the antigens and the antibodies, the presence of binding indicating the presence of a current H. capsulatum infection in the subject, wherein the antigen is one of the antigens described above.

DESCRIPTION OF THE PREFERRED EMBODIMENTS

The present invention may be understood more readily by reference to the following detailed description of the preferred embodiments of the invention, and to the Example and Sequence Listing included therein.

Definitions

The phrases "specific to" and "unique to" the fungus H. capsulatum as used herein in relation to an antigen means that the antigen (an antigenic polypeptide or polypeptide fragment) contains at least one epitope which is not common to other related fungi or other microorganisms (i.e., it is unique to the fungus H. capsulatum), and binds with a higher affinity to antibodies generated against antigens of the fungus H. capsulatum than with antibodies generated against other related fungi or microorganisms. Thus, such an antigen can be distinguished from other antigens by such higher binding affinity. The phrases "specific to" and "unique to" the fungus H. capsulatum as used herein in relation to a nucleic acid or nucleic acid fragment means a nucleic acid or nucleic acid fragment which is not common to other related fungi or other microorganisms (i.e., it is only present in the fungus H. capsulatum).

The phrase "fully complementary" as used herein refers to a nucleic acid which is both the same length as, and exactly complementary in base pairing to, a given nucleic acid.

The phrase "fluid or tissue sample" as used herein means any sample of fluid, or of solubilized or nonsolubilized tissue, obtained from a subject, or solubilized or nonsolubilized cultured cells, which contains components, such as nucleic acids, antibodies or antigens, or fragments thereof, which may be employed in one of the tests described herein to detect a previous or current infection by, or exposure to, the fungus H. capsulatum, or to make a positive diagnosis of histoplasmosis. Such fluid or tissue samples include blood, serum, plasma, sputum, urine, mucus, saliva, gastric juice, lymph, feces, or other bodily fluids, and tissues from the lungs, spleen, liver, skin or other organs. The tissue or fluid samples can also be supernatant from incubated tissue samples or cultured cells.

The term "fragment" as used herein in relation to a polypeptide means a subsequence of the polypeptide which is of a sufficient size and conformation to remain immunogenic (i.e., to have at least one epitope) and/or to produce swelling of the skin of a subject in a skin test for histoplasmosis. The term "fragment" as used herein in relation to a nucleic acid means a subsequence of the nucleic acid which is of a sufficient size and confirmation to properly function as a hybridization probe, as a primer in a polymerase chain reaction, to code for a polypeptide or polypeptide fragment, or in another manner characteristic of nucleic acids.

The term "hybridization" as used herein refers to the formation of a duplex structure by two single-stranded nucleic acids due to fully (100%) or less than fully (less than 100%) complementary base pairing. Hybridization can occur between fully complementary nucleic acid strands, or between less than fully complementary nucleic acid strands which contain regions of mismatch due to one or more nucleotide substitutions, deletions or additions.

The terms "immunogenic" and "antigenic" as used herein mean that a polypeptide, or a fragment thereof, elicits a protective immune response, for example, the production of antibodies against the polypeptide, or fragment thereof, in a subject to which it is administered. The polypeptide or polypeptide fragment will have at least one epitope present therein.

The term "isolated" means that the nucleic acids, nucleic acid fragments, polypeptides, polypeptide fragments or antibodies are of sufficient purity so that they may be employed, and will function properly, in a clinical, diagnostic, experimental or other procedure, such as an immunoassay, a hybridization assay, an amplification reaction, or a skin test for histoplasmosis. Many procedures are known by those of ordinary skill in the art for purifying nucleic acids, nucleic acid fragments, polypeptides, polypeptide fragments and antibodies from other proteins, contaminants, and materials with which they may normally be associated prior to their use in various procedures. For example, the M antigen of *H. capsulatum* obtained from histoplasmin may be purified by standard chromatography procedures, such as cation-exchange chromatography or anion-exchange chromatography, to remove other antigens (c and h antigens, etc.) and proteins, and other components, of histoplasmin therefrom. Recombinantly-produced *H. capsulatum* M antigen may be purified by bound nickel-ion exchange chromatography, or by a combination of Fast Protein Liquid Chromatography (FPLC) using size exclusion chromatography and anion and/or cation exchange chromatography.

Abbreviations for “nucleotides” used herein follow the nomenclature described by the Nomenclature Committee for the International Union of Biochemistry, “Nomenclature for Incompletely Specified Bases in Nucleic Acid Sequences,” *Eur. J. Biochem.* 150:1–5 (1985), in which “A” represents adenine residues, “C” represents cytosine residues, “T” represents thymine residues, “G” represents guanine residues, “I” represents deoxyinosine residues, “M” represents adenine or cytosine residues, “R” represents adenine or guanine residues and “Y” represents cytosine or thymine residues.

The terms “nucleic acid” and “oligonucleotide” include polydeoxyribonucleotides (containing 2-deoxy-D-ribose), polyribonucleotides (containing D-ribose), and to any other type of polynucleotide which is an N glycoside of a purine or pyrimidine base, or modified purine or pyrimidine base. The terms “nucleic acid” and “oligonucleotide” are used interchangeably herein. These terms refer only to the primary structure of the molecule. Thus, these terms include double- and single-stranded DNA, as well as double- and single-stranded RNA. Nucleic acids and oligonucleotides can be prepared by any of several well-known methods. For example, they may be prepared by cloning and restriction of desired sequences, or by direct chemical synthesis by the phosphotriester methods described by Narang et al., *Meth. Enzymol.* 68:90–99 (1979) and Brown et al., *Meth. Enzymol.* 68:109–151 (1979); by the diethylphosphoramidite method described by Beaucage et al., *Tetrahedron Lett.* 22:1859–1862 (1981); or by the solid support method described in U.S. Pat. No. 4,458,066. A review of nucleic acid syntheses methods is provided in Goodchild, *Bioconjugate Chemistry* 1(3):165–187 (1990).

The term “polypeptide” as used herein means a sequence of four or more amino acids which is immunogenic and/or produces swelling of a subject’s skin in a skin test for histoplasmosis, for example the M antigen protein of *H. capsulatum*. The sequence of four or more amino acids can be modified, for example, by chemical, enzymatic or other treatment which does not diminish the immunogenic activity of the polypeptide to any substantial extent.

The phrase “recombinant DNA techniques” as used herein means well-known techniques which permit the isolation and propagation of individual genes, such as the M antigen gene of *H. capsulatum*, and the efficient expression of their products, such as the M antigen of *H. capsulatum*, by plasmid or other expression vectors in various bacterial, yeast or mammalian host expression systems. General information concerning recombinant DNA techniques is present, for example, in Rodriguez et al., Recombinant DNA Techniques: An Introduction (The Benjamin/Cummings Publishing Company, Inc., Menlo Park, Calif., 1983), in Maniatis et al., *Molecular Cloning: A Laboratory Manual* (Cold Spring Harbor Laboratory, Cold Spring Harbor, N.Y., 1982), and in Ausubel et al., *Current Protocols in Molecular Biology*, Greene Publishing Associates and Wiley-Interscience, (John Wiley and Sons, New York (1987; updated quarterly)). The phrase “recombinantly-produced” as used herein means produced by recombinant DNA techniques.

The term “substantially the same as” in relation to the nucleotide sequence set forth in the Sequence Listing as SEQ ID NO:1, or to the nucleotide sequence fully complementary thereto, refers to a nucleic acid having a nucleotide sequence which is similar to the nucleotide sequence set forth in the Sequence Listing as SEQ ID NO:1, or to the nucleotide sequence which is fully complementary thereto, and which retains the functions of such nucleic acid, but which differs from such nucleic acid by the substitution, deletion and/or addition of one or more nucleotides, and/or by the incorporation of some other advantageous feature into the nucleic acid, such as a radio label or other label (biotin, etc.) for nucleic acid detection or immobilization. For example, the essential structure and function of a polypeptide or polypeptide fragment encoded by a nucleic acid which is substantially the same as the above nucleic acids should be the same as the structure and function of a polypeptide or polypeptide fragment encoded by the above nucleic acids. Generally, these nucleic acids will have a nucleotide sequence which has less than about 10% divergence from the nucleotide sequence set forth in the Sequence Listing as SEQ ID NO:1, or from the nucleotide sequence which is fully complementary thereto. Preferably, the nucleic acids will have about 90%, or more preferably about 95%, or even more preferably about 99% homology with the nucleotide sequence set forth in the Sequence Listing as SEQ ID NO:1, or with the nucleotide sequence fully complementary thereto.

Due to the degeneracy in the genetic code, a sequence of three nucleotides (a codon) codes for each of the twenty natural amino acids. However, because there are twenty amino acids and sixty-four possible codons, most amino acids are specified by more than one codon. Thus, the nucleotide sequence of the *H. capsulatum* M antigen gene may be varied from the nucleotide sequence set forth in the Sequence Listing as SEQ ID NO:1, and the nucleotide sequence which encodes the *H. capsulatum* M antigen may be varied from the nucleotide sequence which is fully complementary to the nucleotide sequence set forth in the Sequence Listing as SEQ ID NO:1. Thus, nucleic acids within the present invention are not limited to nucleic acids having a nucleotide sequence as set forth in the Sequence Listing as SEQ ID NO:1, or having a nucleotide sequence fully complementary thereto.

The nucleic acids of the present invention will have the ability of the nucleic acid whose nucleotide sequence is set forth in the Sequence Listing as SEQ ID NO:1, or whose nucleotide sequence is fully complementary thereto, to encode the *H. capsulatum* antigen gene, or M antigen product of this gene, with the M antigen being specific to *H. capsulatum* and being antigenic (being able to stimulate the production of antibodies against the antigen). Alternatively, the nucleic acids of the present invention will have the ability to function as hybridization probes, or as primers in amplification reactions, for the detection of *H. capsulatum*.

Modifications at the 5'-end of a nucleic acid can include, for example, the addition of an isotope, such as $^{32}P$, or a chemical, such as digoxigenin, for detection when using a commercial kit, such as the Boehringer-Mannheim Dig/Genius detection system. In addition, restriction enzyme sites and/or cloning sites can be added to the 5'-end of a nucleic acid (from about 6 to more than about 12 nucleotides) for the direct cloning of the amplified product.

The phrases "target region" and "target nucleic acid" refer to a region of a nucleic acid which is to be amplified, detected, or otherwise analyzed. The sequence to which a primer hybridizes is referred to as a "target sequence."

Nucleic Acids

In one aspect, the present invention provides nucleic acids which are specific to the fungus *H. capsulatum*.

Examples of the nucleic acids of the present invention include a DNA having the nucleotide sequences set forth in the Sequence Listing as SEQ ID NO:1, an RNA having a nucleotide sequence which is fully complementary to the DNA nucleotide sequence set forth in the Sequence Listing as SEQ ID NO:1, and fragments of the foregoing nucleic acids.

Modified Nucleic Acids

Nucleic acids within the present invention also include nucleic acids which are substantially the same as the nucleic acids having the nucleotide sequence set forth in the Sequence Listing as SEQ ID NO:1, or the nucleotide sequence which is fully complementary to the nucleotide sequence set forth in the Sequence Listing as SEQ ID NO:1.

Modifications to a nucleic acid having a nucleotide sequence as set forth in the Sequence Listing as SEQ ID NO:1, or to a nucleic acid having a nucleotide sequence which is complementary to the nucleotide sequence set forth in the Sequence Listing as SEQ ID NO:1, such as one or more nucleotide substitutions, additions, and/or deletions, or the addition of some beneficial component to the nucleic acid, such as a radiolabel or non-radiolabel for nucleic acid detection or immobilization, can be made so long as the nucleic acids do not lose their ability to function in one of the manners described herein. Such modified nucleic acids are within the scope of the present invention if they have the ability to function to encode the *H. capsulatum* M antigen gene, to encode an antigenic polypeptide which is specific to *H. capsulatum*, to function as a nucleic acid probe in a hybridization assay for the detection of *H. capsulatum*, to function as a primer in a polymerase chain reaction used to detect *H. capsulatum*, or to function in some other manner which is characteristic of nucleic acids.

Computer programs are readily available to the skilled artisan which can be used to compare modified nucleotide sequences to previously published nucleotide sequences of *H. capsulatum* to select appropriate sequences for use. A computerized comparison of modified sequences with known sequences catalogued in GENBANK, a computerized database, may be made using the commercially-available computer programs DNASIS (Hitachi Engineering, Inc.), Word Search or FASTA of the Genetics Computer Group (Madison, Wis.), which search the catalogued nucleotide sequences for similarities to the nucleic acid in question.

Nucleic Acid-Based Assay Techniques

The nucleic acids of the present invention can be used to detect a current *H. capsulatum* infection in a sample by any of a number of well-known nucleic acid-based detection techniques, such as hybridization techniques, polymerase chain reaction (PCR), reverse transcription polymerase chain reaction (RT-PCR), ligase chain reaction (LCR), nucleic acid sequencing techniques, electrophoretic and non-electrophoretic identification of nucleic acids, and the like. Alternatively, these nucleic acids can also be used in vectors to safely produce large quantities of the *H. capsulatum* M antigen in suitable host cells for use in the immunodiagnostic techniques and skin tests for histoplasmosis described herein. Thus, the nucleic acids of the present invention, which can vary in length, can be used as probes in nucleic hybridization assays for the detection of *H. capsulatum*, or as primers in polymerase chain reactions for the detection of *H. capsulatum*. It is also contemplated that the nucleic acids of the present invention can be labeled or tagged for use in radioactive, chemiluminescence, fluorescent, or other detection systems.

*H. capsulatum* infection in a tissue or fluid sample suspected of containing *H. capsulatum* infection may be detected by detecting nucleic acids of *H. capsulatum*. Based upon the nucleotide sequence set forth in SEQ ID NO:1, one can design reagents by known methods to detect the presence of *H. capsulatum* in a sample. For example, DNA or RNA obtained from a sample suspected of containing *H. capsulatum* can be sequenced by known methods, and the sequence compared to the nucleotide sequence set forth in SEQ ID NO:1. If the sequence of DNA or RNA obtained from the sample has greater than about 10% divergence from the nucleotide sequence set forth in the Sequence Listing as SEQ ID NO:1, or from a nucleotide sequence complementary thereto, then the sample does not contain *H. capsulatum*. Otherwise (if there is about 90% or more sequence similarity between DNA or RNA obtained from the sample and the nucleotide sequence set forth in the Sequence Listing as SEQ ID NO:1, or the nucleotide sequence complementary thereto), a positive diagnosis of current infection in the sample by the fungus *H. capsulatum* can be made. The above-described computer programs may be used to make the nucleotide sequence comparisons.

Amplification reactions can also be used for detecting *H. capsulatum* infection in a sample. DNA obtained from the sample can be amplified using nucleic acid primers specific to *H. capsulatum*, and detecting the presence of a nucleic acid which is unique to *H. capsulatum*. The presence of a nucleic acid which is unique to *H. capsulatum* indicates the presence of *H. capsulatum* in the sample. The detection of a nucleic acid which is unique to *H. capsulatum* can be by the detection of amplification product when *H. capsulatum*-specific primers are used. The detection of a nucleic acid unique to *H. capsulatum* can be performed by direct hybridization utilizing a *H. capsulatum-specific* oligonucleotide probe, or by a restriction fragment length polymorphism. The primers (and probes) can, for example, be derived from the nucleotide sequence set forth in the Sequence Listing as SEQ ID NO:1, or the sequence complementary thereto. Particularly useful regions of the nucleotide sequence set forth in the Sequence Listing as SEQ ID NO:1 for such purpose are (1) the DNA at the amino terminus encoding amino acids 1–24 of the M antigen, or the sequence complementary thereto; and (2) the DNA at the carboxy terminus encoding amino acids 601–707 of the M antigen, or the sequence complementary thereto. Standard criteria for the selection of sequences for primer development are applicable. The crucial requirement is that the primers be such that an amplification protocol using them can distinguish *H. capsulatum* nucleic acids from the nucleic acids of other fungi, and other microorganisms. While non-specific amplification may also occur, the skilled artisan can distinguish non-specific amplification from the amplification of nucleic acids of *H. capsulatum*, for example, by following amplification with the use of a specific probe derived from the nucleotide sequence set forth in the Sequence Listing as SEQ ID NO:1, or to a sequence fully complementary thereto.

For such uses, the nucleic acids are typically between about 10 and about 100 nucleotides in length, preferably between about 12 and about 30 nucleotides in length, and most preferably between about 15 and about 25 nucleotides in length. There is no standard length for optimal hybridization or polymerase chain reaction amplification. An optimal length for a particular primer application may be readily determined in the manner described in H. Erlich, *PCR Technology, Principles and Application for DNA Amplification*, (1989). Several computer software programs are available to facilitate primer design, for example, Lowe, "Computer Program for Selection of Oligonucleotide Primers for Polymerase Chain Reactions," *Nucl. Acids. Res.* 18:1757–1761 (1991) and *RT-PCR, Methods and Applications Book* 1, (Clontech Laboratories, Inc. (1991)).

In particular, an isolated nucleic acid that selectively hybridizes with (or selectively amplifies) the nucleic acid set forth in SEQ ID NO:1, or the nucleic acid fully complementary thereto, under stringent conditions, and comprises at least 10 nucleotides complementary to the sequence set forth in SEQ ID NO:1, or the nucleic acid fully complementary thereto, is provided. The hybridizing nucleic acid should have at least about 97% (and preferably about 98% or 99%) complementarity with the segment of the nucleic acid of SEQ ID NO:1, or the nucleic acid fully complementary thereto, to which it hybridizes. As used herein to describe nucleic acids, the term "selectively hybridizes" means that a nucleic acid hybridizes with a particular nucleotide sequence, and not with others, and excludes the occasional randomly hybridizing nucleic acids. The hybridizing nucleic acids can be used, for example, as probes or primers for detecting an isolate of *H. capsulatum* that has the nucleic acid to which the primer or probe hybridizes. Thus, these nucleic acids can be the coding sequence for the *H. capsulatum* M antigen protein, or for fragments thereof, that can be utilized to produce an antigenic protein or protein fragment.

If used as primers, the invention provides compositions including at least two nucleic acids which hybridize with different regions of the target *H. capsulatum* sequence so as to amplify a desired region of the target *H. capsulatum* sequence. Depending on the length of the probe or primer, the target region can range from about 97% complementary bases and full complementarity and still hybridize under stringent conditions. For example, for the purpose of diagnosing the presence of *H. capsulatum* infection, the degree of complementarity between the hybridizing nucleic acid (probe or primer) and the sequence to which it hybridizes (e.g., *H. capsulatum* DNA from a sample) is at least enough to distinguish hybridization with a nucleic acid from related fungi.

In general, the nucleic acids of the present invention may be prepared and tested for the ability to selectively hybridize with a target nucleic acid in the manner described herein, or by modifications thereof, using readily-available starting materials, reagents and equipment.

The polymerase chain reaction (for amplifying DNA) and the reverse transcription polymerase chain reaction (for amplifying cDNA generated from RNA) are rapid methods for increasing the copy number of, and sensitively detecting, specific nucleic acid sequences. These methods may be used for the rapid detection of *H. capsulatum* from clinical samples.

The nucleic acids present in a sample which are being amplified may be a single- or double-stranded DNA or RNA. If the starting material is RNA, reverse transcriptase is used to prepare a first strand cDNA prior to conventional polymerase chain reaction.

General information concerning polymerase chain reaction, and the amplification of specific sequences of nucleic acids, is present in U.S. Pat. No. 4,683,195; U.S. Pat. No. 4,683,202; U.S. Pat. No. 4,965,188; U.S. Pat. No. 5,578,467; U.S. Pat. No. 5,545,522; U.S. Pat. No. 5,624,833; Ausubel et al., *Current Protocols in Molecular Biology*, supra.; Rotbart, "Enzymatic RNA Amplification of the Enteroviruses," *J. Clin. Microbiol.* 28:438–442 (1990); Kawasaki, "Amplification of RNA," 21–27, in M. Innis et al., *PCR Protocols* (Academic Press, New York (1990)); and Rossolini et al., "Use of Deoxyinosine-Containing Primers vs. Degenerate Primers for Polymerase Chain Reaction Based on Ambiguous Sequence Information," *Mol. Cell Probes* 8:91–98 (1994). The amplification of cDNA generated from RNA using a reverse transcription/polymerase chain reaction is described in U.S. Pat. No. 5,310,652 and U.S. Pat. No. 5,322,770. Commercial vendors, such as Perkin Elmer (Norwalk, Conn.), market polymerase chain reaction reagents and equipment and publish suitable protocols.

In each cycle of an amplification reaction, a double-stranded target nucleic acid sequence present in a sample is denatured and, due to the presence of a large molar excess of the primers, primers are annealed to each strand of the denatured target sequence. The primers, oriented with their 3' ends pointing towards each other, hybridize to opposite strands of the target sequence and, due to the action of DNA polymerase, prime enzymatic extension along the nucleic acid template in the presence of the four deoxyribonucleotide triphosphates. The two primers anneal to opposite ends of the target nucleic acid sequence, and in orientations such that the extension product of each primer is a complementary copy of the target nucleic acid sequence and, when separated from its complement, can hybridize to the other primer. The end product is then denatured again for another cycle. After this three-step cycle has been repeated between about 25 and 40 times, amplification of a nucleic acid segment by more than one million-fold can be achieved. Each cycle, if 100% efficient, would result in a doubling of the number of target sequences present, thereby leading to exponential increases in the concentration of desired nucleic acid sequences. Better amplification is generally obtained when both primers are approximately the same length.

Denaturation of nucleic acid strands usually takes place at about 94° C. The normal annealing (55 to 60° C.) and extension (65 to 72° C.) temperatures generally used for in vitro amplification by polymerase chain reaction may be used. Examples of suitable reaction times are from about 30 seconds to about 1 minute denaturing; from about 30 seconds to about 1 minute of annealing; and from about 30 seconds to about 2 minutes of extension. One of ordinary skill in the art can, of course, easily determine optimum reaction times and conditions using conventional techniques.

Suitable assay formats for detecting amplification products or hybrids formed between probes and target nucleic acid sequences in a sample are described, for example, in Ausubel et al., *Current Protocols in Molecular Biology*, supra., and in Sambrook et al., *Molecular Cloning-A Laboratory Manual*, Cold Spring Harbor Laboratory, Cold Spring Harbor, N.Y. (1985). Examples of these assay formats include the dot-blot and reverse dot-blot assay formats. In a dot-blot format, amplified target DNA is immobilized on a solid support, such as a nylon membrane. The membrane-target complex is incubated with labeled probe under suitable hybridization conditions, unhybridized probe is removed by washing under suitable stringent conditions, and the membrane is monitored for the presence of bound probe. In a "reverse" dot-blot format, in which the amplified target DNA is labeled and the probes are immobilized on a solid support (e.g., nylon membrane). The target DNA is typically labeled during amplification by the incorporation of labeled primers therein. One or both of the primers can be labeled. The membrane-probe complex is incubated with the labeled amplified target DNA under suitable hybridization conditions, unhybridized target DNA is removed by washing under suitably stringent conditions, and the filter is then monitored for the presence of bound target DNA.

"Stringent conditions" refers to the hybridization conditions used in a hybridization protocol, for example, DNA/DNA hybridization, or in the primer/template hybridization in a PCR reaction. In general, these conditions should be a combination of temperature and salt concentration for washing chosen so that the denaturation temperature is approximately 5–20° C. below the calculated $T_m$ (melting/denaturation temperature) of the hybrid under study. The temperature and salt conditions are readily determined empirically in preliminary experiments in which samples of reference DNA are hybridized to the primer nucleic acid of interest, and then amplified under conditions of different stringencies. The stringency conditions are easily tested, and the parameters altered will be apparent to one skilled in the art. For example, $MgCl_2$ concentrations used in the reaction buffer can be altered to increase the specificity with which the primer binds to the template, but the concentration range of this compound used in hybridization reactions is narrow and, therefore, the proper stringency level is easily determined. For example, hybridizations with oligonucleotide probes 18 nucleotides in length can be done at 5–10° C. below the estimated $T_m$ in 6×SSPE, then washed at the same temperature in 2×SSPE. (See, e.g., Sambrook et al., Molecular Cloning: A Laboratory Manual, supra.) The $T_m$ of such an oligonucleotide can be estimated by allowing 2° C. for each A or T nucleotide, and 4° C. for each G or C. An 18 nucleotide probe of 50% G+C would, therefore, have an approximate $T_m$ of 54° C. Likewise, the starting salt concentration of an 18 nucleotide primer or probe would be about 100–200 mM. Thus, stringent conditions for such an 18 nucleotide primer or probe would be a $T_m$ of about 54° C., and a starting salt concentration of about 150 mM, and modified accordingly by preliminary experiments. $T_m$ values can also be calculated for a variety of conditions utilizing commercially available computer software (e.g., OLIGO®).

Conventional techniques of molecular biology and nucleic acid chemistry which may be employed in the preparative and testing processes of the present invention are fully explained in the literature. See, for example, Ausubel et al., *Current Protocols in Molecular Biology*, supra. Sambrook et al., *Molecular Cloning-A Laboratory Manual*, supra.; Watson et al., *Molecular Biology of the Gene* (Fourth Edition, The Benjamin/Cummings Publishing Company, Inc. 1987); *Oligonucleotide Synthesis* (M. J. Gait, ed., 1984); and *Nucleic Acid Hybridization* (B. D. Hames and S. J. Higgins. eds., 1984).

Vectors and Hosts

The present invention also provides a vector comprising a nucleic acid having the nucleotide sequence set forth in the Sequence Listing as SEQ ID NO:1, having a nucleotide sequence which is substantially the same as the nucleotide sequence set forth in the Sequence Listing as SEQ ID NO:1, a nucleic acid complementary to, or capable of hybridizing with, either of the foregoing nucleic acids, or a fragment of any of the foregoing nucleic acids. The vectors of the invention can be placed into a host (e.g., cell line or transgenic animal) that can express the polypeptides and polypeptide fragments of the present invention.

The *H. capsulatum* M antigen gene (and other nucleic acids within the invention) can be cloned into suitable expression vectors by linking the gene to a suitable promoter in a replicable vector, and expressed in various bacterial, yeast or mammalian host expression systems, as is described in the Example, to safely produce large quantities of the *H. capsulatum* M antigen by propagating the vector in the host under conditions conducive to protein expression. Using conventional techniques, a DNA sequence containing the *H. capsulatum* M antigen gene can be cloned from *H. capsulatum* genomic DNA. The DNA can be converted to double-stranded DNA using cloning techniques well known in the art, including PCR techniques. Linkers or tails may be placed on the ends of the double-stranded DNA to provide convenient restriction sites. After restriction digestion, the DNA may be introduced to any site in a vector, such as a plasmid vector, which has been restricted with a restriction enzyme which generates compatible ends. Following ligation, by means of standard techniques, the DNA can then be introduced into a suitable host system, where it can be expressed to produce the desired *H. capsulatum* M antigen protein.

If desired, the coding sequence for the *H. capsulatum* M antigen gene can be subjected to site-specific mutagenesis, in the manner discussed by Maniatis et al., *Molecular Cloning: A Laboratory Manual*, supra., to alter selected base pairs. Oligonucleotides containing a mutation to be introduced to the cloned gene can be synthesized by well-known DNA synthetic techniques, preferably by phosphoramidite chemistry, and preferably as implemented on an automated synthesizer, such as the synthesizer commercialized by Applied Biosystems.

There are numerous *E. coli* expression vectors known to those of ordinary skill in the art which are useful for the expression of the polypeptides and polypeptide fragments of the invention. Other microbial hosts suitable for such use include bacilli, such as *Bacillus subtilis*, and other enterobacteriaceae, such as *Salmonella, Serratia* and various *Pseudomonas* species. In these prokaryotic hosts, one can also make expression vectors which contain expression control sequences compatible with the host cell, such as an origin of replication. In addition, any number of a variety of well-known compatible promoters will be present, such as a lactose promoter system, a tryptophan (Trp) promoter system, a beta-lactamase promoter system, or a promoter system from phage lambda. The promoters will typically control expression, optionally with an operator sequence, and have ribosome binding site sequences for initiating and completing transcription and translation. If necessary, an amino terminal methionine can be provided by the insertion of a Met codon 5' in-frame with the polypeptide or polypeptide fragment. Also, the carboxyl-terminal extension of the antigen can be removed using standard oligonucleotide mutagenesis procedures.

Additionally, yeast expression systems can be used for the recombinant production of the polypeptide or polypeptide fragment. There are several advantages to the use of yeast expression systems for this purpose. First, evidence exists that proteins produced in a yeast secretion system generally exhibit correct disulfide pairing. Second, post-translational glycosylation is generally efficiently carried out by yeast secretory systems. The *Saccharomyces cerevisiae* pre-pro-alpha-factor leader region (encoded by the MFα-1 gene) is routinely used to direct protein secretion from yeast. (See, for example, Brake et al., "α-Factor-Directed Synthesis and Secretion of Mature Foreign Proteins in *Saccharomyces cerevisiae*," *Proc. Nat. Acad. Sci.* 81:4642–4646 (1984)). The leader region of pre-pro-alpha-factor contains a signal peptide and a pro-segment which includes a recognition sequence for a yeast protease encoded by the KEX2 gene. This enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon, which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

Mammalian cells permit the expression of proteins in an environment which favors important post-transitional modifications, such as folding and cysteine pairing, the addition of complex carbohydrate structures, and the secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen coding sequence can be introduced, for example, into a Chinese hamster ovary cell line using a methotrexate resistance-encoding vector. The presence of the vector DNA in transformed cells can be confirmed by Northern blot analysis, and the production of an opposite strand RNA corresponding to the antigen coding sequence can be confirmed by Southern blot analysis. A number of other suitable host cell lines capable of secreting intact human proteins have been developed, and include the CHO cell lines, HeLa cells, myeloma cell lines, Jurkat cells, and the like. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus and Bovine Papilloma Virus. The vectors containing the nucleic acid segments of interest can be transferred into the host cells by well-known methods, which vary depending upon the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, such as those which are similar to the vectors developed for the expression of human gamma-interferon, tissue plasminogen activator, clotting Factor VIII, hepatitis B virus surface antigen, protease Naxinl, and eosinophil major basic protein, can also be employed. Further, the vector can include CMV promoter sequences and a polyadenylation signal available for expression of inserted nucleic acid in mammalian cells, such as COS7.

The nucleic acid sequences can be expressed in hosts after the sequences have been operably linked, i.e., positioned, to ensure the functioning of an expression control sequence. These expression vectors are typically replicable in the host organisms either as episomes, or as an integral part of the host chromosomal DNA. Commonly, expression vectors can contain selection markers, e.g., tetracycline resistance or hygromycin resistance, to permit detection and/or selection of those cells transformed with the desired nucleic acid sequences. (See, for example, U.S. Pat. No. 4,704,362).

Nucleic acids encoding a variant polypeptide may include sequences which facilitate transcription (expression sequences) and translation of the coding sequences, such that the encoded polypeptide product is produced. Construction of such nucleic acids is well known in the art. For example, such nucleic acids can include a promoter, a transcription termination site (polyadenylation site in eukaryotic expression hosts), a ribosome binding site and, optionally, an enhancer for use in eukaryotic expression hosts and sequences necessary for replication of a vector.

Antigens and Methods

The antigens of the present invention, and monoclonal or polyclonal antibodies raised or generated against these antigens, are useful as diagnostic reagents for detecting the presence of the fungus *H. capsulatum* in a sample, the presence of a previous or current infection by *H. capsulatum*, and for diagnosing histoplasmosis.

Numerous assay techniques based upon immunological reactions between antigens and antibodies may be performed with the antigens and antibodies of the invention to detect the presence of *H. capsulatum* in a sample, the presence of a previous or current infection by *H. capsulatum*, and for making a positive diagnosis of histoplasmosis, including the well-known enzyme-linked immunosorbent assays (ELISA), immunofluorescence assays (IFA), radioimmuno assays, immunoelectrophoresis, immunoblotting and the like.

Using any of the known assay techniques which are based upon immunological reactions, a previous or current *H. capsulatum* infection in a subject may be detected by the steps comprising: (a) contacting a fluid or tissue sample from the subject which contains antibodies with an isolated or recombinantly-produced antigen of the present invention; and (b) detecting the presence of binding between the antibodies and the antigen, the presence of binding indicating the presence of a previous or current *H. capsulatum* infection in the subject.

In these immunodiagnostic techniques, the antigen employed can be any of the isolated or recombinantly-produced polypeptides or polypeptide fragments described hereinabove. Because large quantities of polypeptides and polypeptide fragments can be safely produced by recombinant DNA techniques using nucleic acids described herein, and purified, it is preferable to use recombinantly-produced polypeptides and polypeptide fragments in the immunodiagnostic techniques of the invention.

The nucleotide sequence which is complementary to the DNA nucleotide sequence set forth in the Sequence Listing as SEQ ID NO:1 encodes the *H. capsulatum* M antigen. Thus, the antigen employed in the immunoassay techniques described herein can be this protein, an antigenic polypeptide fragment of this protein, or any other antigenic polypeptide or polypeptide fragment encoded by nucleic acid which has a nucleotide sequence which is complementary to SEQ ID NO:1, or to a nucleic acid which has a nucleotide sequence which is substantially the same as the nucleotide sequence which is complementary to SEQ ID NO:1. It is already well established that the *H. capsulatum* M antigen is antigenic, and is specific for *H. capsulatum*. Fragments of the *H. capsulatum* M antigen may also possess one or more epitopes of the M antigen protein which are unique to *H. capsulatum*. These epitopes, and the polypeptides and polypeptide fragments containing them, can be readily determined by the well-known techniques of epitope mapping and conformational dependency analysis. Monoclonal antibodies directed against the M antigen may be utilized, as described in Zancopé-Oliveira et al., "Evaluation of Cation Exchange Chromatography for Purifying the M-glycoprotein Antigen from Histoplasmin," *J Med Vet Mycol* 31, 29–41 (1993), and Zancopé-Oliveira et al., "Immunochemical Analysis of Glycosidic Epitopes in the H and M Antigens from *Histoplasma capsulatum*," *Clinical and Diagnostic Laboratory Immunology*, 1: 563–568 (1994). The monoclonal antibodies can be applied in the enzyme-linked immunoelectrotransfer blot (western blot) method. In addition, partial digestion with proteinases can be utilized to fragment recombinant M antigen. The fragments can be purified by Fast Protein Liquid Chromatography (FPLC), and used in an intermediate gel to inhibit the immune precipitation of M antigen by specific antiserum in 2 dimensional crossed rocket immunoelectrophoresis. Further, a phage display library with restriction endonuclease digested M antigen gene can be developed. The phages expressing peptides can be tested by replica plating for immunoreactivity by indirect enzyme immunoassay. By testing homologous antisera and monoclonal antibodies, and those obtained from heterologous fungi, one can determine which peptide fragments contain epitopes specific for *Histoplasma capsulatum*.

Polypeptides which may be employed in the immunodiagnostic assays and skin tests of the present invention are those encoded by the plus strands of the nucleic acids of the invention. Antigenic fragments of the polypeptides can be synthesized directly, or obtained by chemical or mechanical disruption of the fungus, or of the larger polypeptides. The antigenic polypeptides and polypeptide fragments of the present invention can also be recombinant proteins, polypeptides or fragments thereof, obtained by cloning nucleic acids encoding the proteins, polypeptides or fragments in an expression system capable of producing the antigenic proteins, polypeptides, or fragments thereof.

Using the deduced amino acid sequence of the *H. capsulatum* M antigen set forth in the Sequence Listing as SEQ ID NO:2, it is also possible to synthesize, using standard peptide synthesis techniques, polypeptide fragments chosen to be homologous to immunoreactive regions of the larger antigen, and to modify these fragments by inclusion, deletion or modification of particular amino acids residues in the sequences. The amino acid sequences of the antigens of the invention can contain an immunoreactive region attached to sequences designed to provide for some additional property, such as solubility. These amino acid sequences can also include amino acid substitutions to provide for some additional property, such as to remove or add amino acids capable of disulfide bonding, to increase antigenicity and/or bio-longevity, or to alter enzymatic activity. Thus, synthesis and purification of an extremely large number of polypeptides and polypeptide fragments derived from the *H. capsulatum* M antigen is possible. However, these polypeptides and polypeptide fragments need to have a bioactive property, such as antigenicity.

The isolated polypeptides and polypeptide fragments obtained or produced can be tested to determine their antigenicity (immunoreactivity), immunogenicity and specificity by the well-known methods discussed hereinabove. One example of an immunologic technique that may be used for the detection of current or previous infection by *H. capsulatum* utilizes monoclonal antibodies (MAbs) for detection of antibodies that specifically bind *H. capsulatum* M antigen. Briefly, sera or other body fluid from the subject is reacted with *H. capsulatum* M antigen bound to a substrate (e.g., an ELISA 96-well plate). After excess sera is thoroughly washed away, a labeled (e.g., enzyme-linked, fluorescent, radioactive, or the like) monoclonal antibody is then reacted with the previously reacted antigen-serum antibody complex. The amount of inhibition of monoclonal antibody binding is measured relative to a control (no patient serum antibody).

The isolated or recombinantly-produced antigens of the invention can also be used as skin test antigens in skin tests for histoplasmosis. These skin tests are performed in a manner known by those of skill in the art for this disease, and for other pulmonary diseases, such as tuberculosis. Generally, a small quantity (generally about 0.1 ml) of liquid, such as physiological saline, containing an antigen of the invention, such as the *H. capsulatum* M antigen, is injected intradermally beneath the skin (on the forearm or other convenient location) of a patient, and the site of injection is observed at predetermined times, such as 24 and 48 hours post injection, for the presence of swelling of the skin. If no swelling of the skin at the injection site is observed, this indicates that the patient tested was not exposed to *H. capsulatum*. If swelling of the skin at the injection site is observed, this indicates that the patient tested has been exposed to *H. capsulatum*. Skin tests are usually observed, and the area of induration measured, at 24 hours, 48 hours and 72 hours after intradermal injection in the volar surface of the forearm. For general information concerning these skin tests, see Klimas, "Delayed Hypersesntivity Skin Testing," pp. 276–280, in Rose et al., *Manual of Clinical Laboratory Immunology* (5th ed., eds. American Society for Microbiology, Washington, 1996). For general information concerning the use of *H. capsulatum* glycoproteins in a skin test for the diagnosis of histoplasmosis, see Sprouse, "Determination of Molecular Weight, Isoelectric Point, and Glycoprotein Moiety for the Principal Skin Test-Reactive Component of Histoplasmin," *Infection and Immunity* 15, 263–271 (1977).

Prior to using the isolated or recombinantly-produced antigens in any immunodiagnostic assays or skin tests, it is preferable that the antigens be partially or fully deglycosylated by, for example, mild periodate oxidation with about 0.025 M sodium meta-periodate at about 4° C. for about 4–8 hours in the dark, followed by reduction with sodium borohydride, and then an equimolar amount of glycerol.

Antibodies

An isolated antibody which binds with antigens of the present invention is also provided. The antibodies can be polyclonal or monoclonal, and should specifically bind an epitope of an antigen which is specific to *H. capsulatum*. The term "bind" means the well-understood antigen-antibody interactions, or other nonrandom association with an antigen. "Specific binding" as used herein means an antibody that has a higher affinity for its target molecule (e.g., an antigen of the invention) than for non-target molecules (e.g., antigens of other closely-related fungi, or of other microorganisms).

Antibodies can be made by many well-known methods. See, for example, Harlow and Lane, *Antibodies: A Laboratory Manual* (Cold Spring Harbor Laboratory, Cold Spring Harbor, N.Y. (1988)). Briefly, an isolated or recombinantly-produced antigen can be injected into an animal in an amount, and in intervals, sufficient to elicit an immune response (i.e., the production of antibodies against the antigen). Antibodies can be obtained from the animal and purified directly by well-known methods. Alternatively, spleen cells can be obtained from the animal, and then fused with an immortal cell line and screened for monoclonal antibody secretion. The antibodies can be used to screen nucleic acid clone libraries for cells secreting the antigen. These positive clones can then be sequenced. The production of a murine monoclonal antibody (EC2–EC7) which is specific to the M antigen of *H. capsulatum* is described in Reiss et al., "Monoclonal Antibodies against the M-protein and Carbohydrate Antigens of Histoplasmin Characterized by the Enzyme-Linked Immunoelectrotransfer Blot Method," *Infection and Immunity*, 53, 540–546 (1986).

Specific examples of isolated antibody within the invention which specifically bind to *H. capsulatum* antigens include antibodies which specifically bind with an isolated or recombinantly-produced polypeptide encoded by a nucleic acid which has a nucleotide sequence which is complementary to SEQ ID NO:1, or to antigenic fragments thereof.

Using any of the known assay techniques which are based upon immunological reactions, a current *H. capsulatum* infection in a subject suspected of having an *H. capsulatum* infection may be detected by the steps comprising: (a) contacting a fluid or tissue sample from the subject which contains antigens with antibodies generated against an antigen of the present invention; and (b) detecting the presence of binding between the antigens and the antibodies, the presence of binding indicating the presence of a current *H. capsulatum* infection in the subject.

General information concerning the reactions of antibodies to antigens of *H. capsulatum* is present in Kumar et al., "Cross-Reacting Human and Rabbit Antibodies to Antigens of *Histoplasma capsulatum, Candida Albicans* and *Saccharomyces Cerevisiae*," Infect. Immun. 48:806–812 (1985); Reiss et al., "Monoclonal Antibodies Against the M Protein and Carbohydrate Antigens of Histoplasmin Characterized by the Enzyme-Linked Immunoelectrotransfer Blot Method," supra.; and Harris, "Characterization of Anigenic Determinants in Histoplasmin that Stimulate *Histoplasma Capsulatum*-Reactive T Cells in Vitro," *Infection and Immunity* 56, 2343–2349 (1988).

Kits

The present invention also provides a kit for detecting a previous or current *H. capsulatum* infection in a sample, or for diagnosing histoplasmosis. Preferably, the kit will contain one or more of the isolated nucleic acids, isolated or recombinantly-produced antigens, or isolated antibodies of the invention, and instructions describing the use of the nucleic acids, antigens or antibodies in the detection of a previous or current *H. capsulatum* infection, or in the diagnosis of histoplasmosis.

Vaccines

The isolated nucleic acids and isolated or recombinantly-produced antigens of the present invention may be used as the active component in an immunogenically-effective amount (an amount which is effective to stimulate the production of antibodies against the nucleic acids or antigens in the particular subject being vaccinated) in a vaccine for the prevention or treatment of histoplasmosis along with a pharmaceutically-acceptable carrier for the nucleic acids or antigens to provide protective resistance against *H. capsulatum*. Such a vaccine would be particularly useful for individuals who are at a high risk for contracting histoplasmosis, such as individuals who explore caves where birds and/or bats may be present, and individuals who deconstruct vacant buildings, which be inhabited by birds and/or bats.

Active immunization can be achieved through natural infection with an organism or virus, or artificially by vaccination. (See, for example, Kuby, *Immunology* (W.H. Freeman and Co., New York (1992)).) It is also contemplated that immunization against disease caused by *H. capsulatum* can be achieved by a "naked" DNA vaccine approach. Briefly, DNA constructs containing promoter sequences upstream of *H. capsulatum* M antigen coding sequences can be injected into muscle tissue or administered via the mucosa and result in expression of antigens that induce a protective immune response.

An immunogenically-effective amount of the nucleic acids or antigens of the invention will generally range from about 100 nanograms to about 1 microgram of the nucleic acids, and from about 10 to about 100 micrograms of the antigens. Immunogenically-effective amounts of the vaccine, nucleic acid or antigen can be determined using standard procedures. Briefly, various concentrations of the nucleic acid or antigen are prepared and administered to an animal, and then the immunological response (e.g., the production of antibodies or cell mediated immunity) of the animal to each concentration is determined. The amounts of nucleic acid or antigen administered depend on the subject, e.g. a human or an animal, the condition of the subject, the size of the subject, etc. Thereafter, the animal so inoculated with the nucleic acid or antigen can be exposed to *H. capsulatum* to test the potential vaccine effect (protective immunogenicity) of the specific nucleic acid or antigen. The specificity of the nucleic acid or antigen can be ascertained by testing sera, other fluids or lymphocytes from the inoculated animal for cross reactivity with other closely-related fungi, or other microorganisms.

The pharmaceutically-acceptable carrier which may be employed in the vaccines can comprise saline or other suitable carriers. See, for example, Arnon, R. (Ed.) *Synthetic Vaccines* (CRC Press, Inc., Boca Raton, Fla. (1987)). By "pharmaceutically-acceptable" is meant a material that may be administered to a subject along with a selected nucleic acid or antigen without causing any undesirable biological effects, or interacting in a deleterious manner with any of the other components of the pharmaceutical composition in which it is contained. The carrier will depend upon the method of administration and choice of adjuvant, if one is used. An adjuvant can also be a part of the carrier of the vaccine, in which case it can be selected by standard criteria based upon the nucleic acid or antigen used, the mode of administration and the subject. Methods of administration can be by oral or sublingual means, or by injection, depending on the particular vaccine used, and the subject to whom it is administered.

The vaccine can be used as a prophylactic or a therapeutic modality. Thus, the invention contemplates methods of preventing or treating infection from *H. capsulatum*, and the associated diseases, by administering the vaccine to a subject.

The following Example describes and illustrates the methods for the cloning and sequencing of the *H. capsulatum* M antigen gene. This Example is intended to be merely illustrative of the present invention, and not limiting thereof in either scope of spirit. Those of skill in the art will readily understand that variations of the reagents used in, and the conditions and processes of, the procedures described in this Example can be Used to clone and sequence nucleic acids which are specific to *H. capsulatum*.

All materials and equipment employed in the Example, and generally employed to make and use the nucleic acids, polypeptides, vaccines and kits of the present invention, are commercially-available. Sources for these materials and equipment are set forth in the Example, or are known by those of skill in the art.

EXAMPLE

Cloning and Sequencing of the *H. capsulatum* Gene Encoding the M Antigen

In these experiments, the gene encoding the M antigen of *H. capsulatum* var. *capsulatum* (anamorph name, but also known by the teleomorph name *Ajellomyces capsulatus*) Centers for Disease Control and Prevention (CDC) strain 6623, which is deposited with the ATCC under Accession Number ATCC 26320, was cloned and sequenced.

Semi-purified M. protein was transferred to PVDF membranes. The eluted protein was sequenced directly, and cleaved with various proteinases, and the internal peptides were sequenced by microbore HPLC. Although the $NH_2$ terminus was blocked, several internal amino acid sequences were obtained. A homology search through a protein data base revealed significant similarity of these amino acid sequences to both eukaryotic and prokaryotic catalases. This degree of conservation facilitated peptide alignments. Degenerate oligonucleotides were constructed in the proper orientation for polymerase chain reactions (PCR). The amino acid sequence derived from the resulting amplicon confirmed that it encoded a region of the M antigen gene. This probe was used to screen an *H. capsulatum* genomic library, and a 4.0 kb fragment containing the entire M antigen gene was cloned and sequenced by the dideoxy chain termination method of Sanger et al., "DNA Sequencing with Chain-Terminating Inhibitors," *Proc. Natl. Acad. Sci USA* 74, 5463–5467 (1977). This gene was found to contain five introns, as determined by sequence analysis of cDNA obtained by reverse transcription polymerase chain reaction, and to be homologous with other members of the catalase family. The nucleotide sequence (DNA) for this M antigen gene, which contains 3862 nucleotides, is set forth in the Sequence Listing as SEQ ID NO:1. For the mature protein (not including a sixteen amino acid leader sequence), the open reading frame starts at base pair number 566 of the genomic clone, and stops at base pair number 2812 thereof. Introns are present in the nucleotide sequence between six exons, which are present at base pair numbers 566–793, 852–1077, 1168–1583, 1706–1870, 1950–2124 and 2208–3121. The sequence of the clone containing the M antigen gene has been deposited in GenBank under accession number AFO 26268.

Materials and Methods

Strains, plasmids and cultures conditions. Yeast-phase cells of *H. capsulatum* strain 6623 (ATCC 26320) were grown at 37° C. in Pine's Liquid Medium for 48 hours to late log phase. *E. coli* strain q358 was used as the host for the bacteriophage l Gem11, and *E. coli* INV aF' (Invitrogen Co., Carlsbad, Calif.) was used as the recipient for the subcloning vector pBluescript SK (Stratagene, La Jolla, Calif.).

Purification of the M antigen. M antigen was purified by tandem cation exchange chromatography in columns of CM Sepharose CL-6B from histoplasmin, as described by Zancopé-Oliveira et al., "Evaluation of Cation Exchange Chromatography for the Isolation of M Glycoprotein from Histoplasmin," supra.

Amino acid sequence of M antigen. Samples of M antigen were electrophoresed on 10% SDS-PAGE, and transferred for 1 hour at 400 mA to polyvinylidene difluotide membranes (Immobilon-P, Milipore Corp., Bedford, Mass.) in 25 mM Tris, 192 mM glycine, and methanol (20% [vol/vol]). The membrane was washed several times with 1 mM DTT, stained with Ponceau S and destained with 10% aldehyde-free acetic acid-1 mM DTT. Several washings with 1 mM DTT were made to remove the acetic acid. The band was identified by its molecular weight, and its identity was confirmed by immunoblotting. The band corresponding to M antigen (200 pmol/protein band) bound to the membrane was excised, and submitted to Edman degradation without any prior modification. To obtain the internal sequences, the band was digested in situ with lysyl endopeptidase (Boehringer Mannheim, Indianapolis, Ind.), and peptides were purified using microbore reverse-phase high-performance liquid chromatography (HPLC) on reverse phase C18 silica. All amino acid sequences were obtained using ABI sequencers (models 477A Protein Sequencer or Procise, Applied Biosystems, Foster City, Calif.) which utilize pulse-liquid chemistry.

DNA isolation. Yeast cells grown in 50 ml of Pine's broth were harvested by filtration on 0.45 µm porosity membrane (Nalgene), washed 3 times with deionized $H_2O$ and blotted to remove excess moisture. Cells were placed in a sterile mortar with approximately 1 g glass beads (0.5 mm), and liquid nitrogen, and were ground to a fine powder. The powder was resuspended in 20 ml of TE Buffer, pH 8.0 (10 mM Tris-1 mM EDTA), and DNA was extracted with phenol, ethanol precipitated, and dried and redissolved in 0.05 M TE. The RNA was removed by the addition of RNAse (10 µg/ml final concentration) (Boehringer Mannheim) at 37° C. for 1 hour, followed by proteinase K treatment (50 µg/ml) (Sigma Chemical Co., St. Louis, Mo.)

for an additional 1 hour at 37° C. The DNA was subjected again to phenol extraction, and EtOH precipitation, and redissolved in TE.

Generation of M DNA probe by PCR. *H. capsulatum* genomic DNA was used to amplify a DNA fragment encoding an internal portion of the M protein by PCR. Degenerated oligonucleotides primers (1 µM) were designed on the basis of two of six internal peptides (V22 and V18) derived from the amino acid sequence of the M antigen, which are set forth in Table 1, because the NH$_2$ terminus appeared to be blocked:

TABLE 1

Amino Acid Sequences of NH$_2$-Terminus and Lysyl Endopeptidase-Digested Fragments of the M Antigen

| Origin | Amino Acid Sequence |
|---|---|
| NH$_2$ terminus | S D P T D Q F L (SEQ ID NO:3) |
| Internal Sequences | |
| 2642-m1947/19 | D F I F R Q K I Q H F D H E R (SEQ ID NO:4) |
| 5070-m1941/20 | T L Q G R A G L V (SEQ ID NO:5) |
| V22-m1947/20 | A Q A L G G K N P D F H R Q D L (SEQ ID NO:6) |
| V21-m1947/12 | S G R Y P E (SEQ ID NO:7) |
| V16-m1941/21 | F D F D L L D P T K (SEQ ID NO:8) |
| V18-m1941/23 | I I P E E L V P F T P I G K (SEQ ID NO:9) |

The sense primer M4F [5'-AA(AG)AA(CT)CC(AGC)GA(CT)TT(CT)-3', SEQ ID NO:10] was a 15-mer with 48-fold degeneracy, and the antisense primer M8R [5'-TT(AGCT)CC(AGT)AT(AGCT)GT(AG)AA-3', SEQ ID NO:11] was a 14-mer with 96-fold degeneracy. PCR was carried out in a total volume of 100 µl containing 100 ng of DNA as template, 100 M each of dNTP, 1 M of each oligonucleotide primer, and 10×PCR Buffer containing 500 mM KCl, 100 m Tris-HCl, pH 8.3, 25 mM MgCl$_2$, and 2.5 U of Taq polymerase (Boehringer Mannheim). The amplification conditions consisted of a denaturation at 95° C. for 5 minutes followed for 35 cycles of the succeeding steps: denaturation at 95° C. for 5 minutes, annealing at 50° C. for 1 minute, and extension at 72° C. for 1 minute. A final elongation was done at 72° C. for 5 minutes. A 300-bp PCR product was subcloned into the pCRII vector using the TA cloning kit (Invitrogen, San Diego, Calif.), and using procedures recommended by the vendor, and sequenced using a dye-labeled terminator and automated sequencer (Applied Biosystems).

Screening of an *H. capsulatum* genomic library. The 300-bp amplicon was labeled with [-$^{32}$P]dCTP by High Prime DNA Labeling Mix (Boehringer Mannheim), purified in a DEAE column (NACS Prepac Convertible—BRL Life Technologies, Inc.), and used for screening the genomic library, derived from DNA partially digested with Sau3A1 and cloned into lGem11 via the Xho 1 half-site. An *E. coli* q358 strain bacterium infected with the genomic library, was replica plated onto nitrocellulose membranes. Plaques were lysed, and then heat fixed. Filters were hybridized with $^{32}$P-labeled probe. Twelve positive colonies were picked, and rescreened as large plaques. Two strongly positive plaques were purified and mapped by Southern analysis. These clones were digested with BamH1 and one fragment of 4.0 kb was obtained.

Gene sequence analysis: The 4.0 kb fragment was subcloned into pBluescript II KS, and sequenced by the strategy of *primer walking* using the dideoxy chain termination method. Oligonucleotides of 22-mer were synthesized on the basis of DNA sequence and applied to initiate the sequence reaction. The clone was sequenced in both directions. To determine the sites of putative introns, 5 µg of RNA was reverse transcribed using oligo-dT to initiate the cDNA reaction. The first strand of cDNA was amplified with a sense primer located at the start site of the mature protein: the sequence of this primer was 5'-CGGAATCCTCCGAC-CCTACGGA-3' (SEQ ID NO:12). The antisense primer was 5'-ACCAAGCTTCTATCCAACGGGAACCGA-3' (SEQ ID NO:13). A 5'EcoRI site (underlined) was added to the sense primer, and a HindIII site (underlined) was added to the antisense primer to facilitate cloning in pBluescript SK-. PCR was performed for 35 cycles of 94° C. for 45 seconds, 50° C. for 45 seconds and 72° C. for 2 minutes with 5 U of Vent polymerase (New England Biolabs, Beverly, Mass.). The PCR product was digested with EcoRI and HindIII and cloned into pBluescript SK-, restriction mapped and sequenced in its entirety. The gene encoding the M antigen was deposited in GenBank, and its accession number is AF026268.

Results

M antigen amino acid sequencing. Peptides sequences of the M antigen were determined after digestion of purified M glycoprotein with lysyl endopeptidase, and purification using high-performance liquid chromatography (HPLC). Undigested antigen and internal peptides were sequenced by Edman degradation. The amino acid sequences of the NH$_2$ terminus and 6 internal peptides are shown in Table 1. The amino acid sequences of two internal peptides, V22 and V18, of the M protein (Table 1) showed 66–73% of identity with sequences of catalases of *Schizosaccharomyces pombe* (gpD55675 YSPC_1) and *Aspergillus niger* (gpZ23138 ANCATRGNA_1).

Cloning and sequencing of the M gene. The significant degree of homology of the two internal peptides V22 and V18 to fungi catalases suggested a certain arrangement in the protein. Considering their positions, two degenerate oligonucleotides (sense primer M4F and antisense primer M8R) were designed, based upon the two internal peptides V22 and V18, respectively, and used in a PCR reaction to amplify a 320 base pair fragment of *H. capsulatum* genomic DNA. A 300 base pair PCR product was achieved using M4F and M8R as primers, and confirmed by Southern blot to represent a unique gene of *H. capsulatum*. Sequence analysis of this 300 base pair amplicon obtained by the dideoxy chain terminator method enclosed the two native internal peptides, confirming that the PCR product encoded a region of the gene encoding the M antigen.

To isolate the entire gene encoding the M antigen, the 300 base pair PCR fragment was gel purified in 1% agarose, and used to screen an *H. capsulatum* genomic DNA library. A BamH1 genomic fragment of 4.0 kb carrying the gene encoding the M antigen was isolated and characterized. This fragment was subcloned into pBluescript II KS, and was sequenced in its entirety in both directions. SEQ ID NO:1 shows the complete nucleotide sequence of the *H. capsulatum* gene encoding the M antigen, and SEQ ID NO:2 shows the deduced amino acid sequence, which consisted of 707 amino acid residues (including a sixteen amino acid leader sequence) with an estimated molecular weight of about 78,172 Da.

The coding region of the M antigen gene is set forth in SEQ ID NO:1. It is interrupted by 5 introns, which begin and end at the base pair numbers 794–851, 1078–1167, 1584–1705, 1871–1949 and 2125–2207, with the 5' and 3' extremities presenting the GT/AG consensus. The 5'-565 base pair flanking sequence of this gene (the 565-base pair sequence directly preceding the first exon (first coding sequence)) exhibited similarity with the promoter regions of eucaryotic genes. A TATA element is present at base pair position 318, and a T+C-rich pyrimidine block is found downstream at base pair position 365. The CAA motif is found twice upstream of the T+C block at base pair positions 34 and 341. The 3'-region downstream from the M antigen gene open reading frame contains a pentanucleotide (5'-AAATA-3') at base pair position 3134, 19 nucleotides downstream from the termination codon. This sequence is similar to the polyadenylation consensus sequence described in eukaryotic organisms. It may play a role in the termination of transcription, processing, and addition of poly(A) at the 3'-terminus.

Protein structure. Sequencing of the N-terminus of the native protein revealed that the first residue of the mature protein is the serine residue at base pair position 566. The mature protein is 691 amino acids with a predicted size of 76,398 Da. Therefore, the expected M antigen gene has a leader peptide composed of 16 amino acids (the 16 amino acids which precede the serine residue at base pair number 566, and which begin with methionine) resulting in an amino acid sequence of 707 amino acids. Five potential N-glycosylation sites (NXT or NXS) were predicted.

Comparison of the amino acid sequence of the M antigen gene with known sequences. The earlier data base results showing that two peptides sequences of M protein had 66–73% of identity with sequences of catalases of *Schizosaccharomyces pombe* (gpD55675 YSPC_1) and *Aspergillus niger* (gpZ23138 ANCATRGNA_1) suggested that the M antigen could be a catalase. Comparison of the M deduced amino acid sequence with known fungal catalases from *Aspergillus fumigatus* (GenBank accession number u87850), *Eimericella nidulans* (GenBank accession number u80672), *Aspergillus niger* (GenBank accession number 115474), and *Saccharomyces cerevisiae* (GenBank accession number x13028), using a Genetics Computer Group, Inc., computer program, demonstrated 61.2, 60.4, 53.2 and 21.7% of similarity at the amino acid level, respectively. The M antigen amino acid sequence can be divided into parts of high and low homology with these other amino acid sequences, which may suggest functional domains.

Copy number of M gene. Southern blot of *H. capsulatum* genomic DNA digested with various restriction enzymes was probed with the 320-base pair PCR product in order to evaluate the genomic organization of the M antigen gene. A single hybridized band of 4.0 kb was seen with the BamHI-digested genomic DNA, which corresponded to the size of the lGem11 purified inserts. The hybridization profile of the other fragments manifested only a single band, suggesting that a single copy or few copies of the M antigen gene could occur in the genome.

The foregoing Example is provided to enable one of ordinary skill in the art to practice the present invention. This example is merely illustrative, however, and should not be read as limiting the scope of the invention as it is claimed in the appended claims.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the invention be limited only by the scope of the claims which follow, and that such claims be interpreted as broadly as is reasonable.

Specific nucleic acids, antigens, antibodies, vaccines, methods and kits within the scope of the invention include, but are not limited to, the nucleic acids, antigens, antibodies, vaccines, methods and kits described herein. Contemplated equivalents of the nucleic acids, antigens, antibodies, vaccines, methods and kits described herein include nucleic acids, antigens, antibodies, vaccines, methods and kits which otherwise correspond thereto, and which have the same general properties thereof, wherein one or more simple variations are made which do not adversely affect the function of the nucleic acids, antigens, antibodies, vaccines, methods and kits as described herein.

The Sequence Listing which is present herein uses the symbols for bases and amino acids which are described in §2423 of the U.S. Patent and Trademark Office *Manual of Patent Examining Procedure*, in which R represents A or G, Y represents C or T/U and V represent A or C or G.

Throughout this application, various patents, publications, books, nucleic acid and amino acid sequences, and computer programs have been cited. The entireties of each of these patents, publications, books, nucleic acid and amino acid sequences, and computer programs are hereby incorporated by reference herein into this application.

What is claimed is:

1. An isolated *Histoplasma capsulatum* M antigen-specific nucleic acid selected from the group consisting of:
    a nucleic acid having a nucleotide sequence as set forth in the Sequence Listing as SEQ ID NO:1;
    a nucleic acid having a nucleotide sequence which is complementary to the nucleotide sequence set forth in the Sequence Listing as SEQ ID NO:1;
    an *H. capsulatum* M antigen-specific fragment of a nucleic acid of SEQ ID NO:1; and
    an *H. capsulatum* M antigen-specific fragment of a nucleic acid with a nucleotide sequence which is complementary to the nucleotide sequence set forth in the Sequence Listing as SEQ ID NO:1;
    wherein the nucleic acid does not contain the nucleotide sequences 5'CGAAGTCGAGGCTTTCAGCATG3' (SEQ ID NO:14), 5'TATTAGCTCTAGAATTAC- CACGGGTATCCAAGTAGTAAGG3' (SEQ ID NO:15), 5'CCCCGAAGGGCATTGGTTTTT- TATCTAATAAATACACCCC3' (SEQ ID NO:16), or nucleotide sequences complementary thereto,
    and wherein the nucleic acid is not a nucleic acid consisting essentially of between 10 and 100 nucleotides which is able to form a hybrid at 60° C. with a nucleotide polymer having a nucleotide sequence of 5'CGAAGTCGAGGCTTTCAGCATG3' (SEQ ID NO:17), 5'CATGCTGAAAGCCTCGACTTCG3' (SEQ ID NO:18), 5'CAUGCUGAAAGCCUCGACU- UCG3'(SEQ ID NO:19) or 5'CGAAGUCGAGGCU- UUCAOCAUG3'(SEQ ID NO:20).

2. The nucleic acid of claim 1, wherein the nucleic acid has the nucleotide sequence set forth in the Sequence Listing as SEQ ID NO:1.

3. The nucleic acid of claim 1, wherein the nucleic acid has a nucleotide sequence which is complementary to the nucleotide sequence set forth in the Sequence Listing as SEQ ID NO:1.

4. The *H. capsulatum* M antigen-specific nucleic acid of claim 1, wherein the nucleic acid is an *H. capsulatum* M antigen-specific fragment of a nucleic acid of SEQ ID NO:1.

5. The *H. capsulatum* M antigen-specific nucleic acid of claim 1, wherein the nucleic acid is an *H. capsulatum* M antigen-specific fragment of a nucleic acid with a nucleotide sequence which is complementary to the nucleotide sequence set forth in the Sequence Listing as SEQ ID NO:1.

6. A vector containing an insert consisting of an *H. capsulatum* M antigen-specific nucleic acid, wherein the nucleic acid has a nucleotide sequence as set forth in the Sequence Listing as SEQ ID NO:1 or consists of an *H. capsulatum* M antigen-specific fragment of a nucleic acid of SEQ ID NO:1, and wherein the vector is suitable for expressing the nucleic acid.

7. The vector of claim 6, wherein the nucleic acid has a nucleotide sequence as set forth in the Sequence Listing as SEQ ID NO:1.

8. The vector of claim 6, wherein the nucleic acid is an *H. capsulatum* M antigen-specific fragment of a nucleic acid of SEQ ID 1.

9. An isolated host cell for expressing a polypeptide, comprising a vector containing a nucleic acid, wherein the vector is suitable for expressing the nucleic acid, and wherein the nucleic acid:
    has a nucleotide sequence as set forth in the Sequence Listing as SEQ ID NO:1; or
    is an *H. capsulatum* M antigen-specific fragment of a nucleic acid of SEQ ID NO:1.

10. The isolated host cell 9, wherein the nucleic acid has a nucleotide sequence as set forth in the Sequencing Listing as SEQ ID NO:1.

11. An isolated nucleic acid consisting of:
    a nucleic acid consisting of a nucleotide sequence as set forth in the Sequence Listing as SEQ ID NO:1;
    a nucleic acid consisting of a nucleotide sequence which is complementary to the nucleotide sequence set forth in the Sequence Listing as SEQ ID NO:1;
    an *H. capsulatum* M antigen-specific nucleic acid which is 90% similar to a nucleic acid consisting of a nucleotide sequence as set forth in the Sequence Listing as SEQ ID NO:1;
    an *H. capsulatum* M antigen-specific nucleic acid which is 90% similar to a nucleic acid consisting of a nucleotide sequence which is complementary to the nucleotide sequence set forth in the Sequence Listing as SEQ ID NO:1;
    an *H. capsulatum* M antigen-specific fragment of a nucleic acid consisting of a nucleotide sequence as set forth in the Sequence Listing as SEQ ID NO:1;
    an *H. capsulatum* M antigen-specific fragment of a nucleic acid consisting of a nucleotide sequence which is complementary to the nucleotide sequence set forth in the Sequence Listing as SEQ ID NO:1;
    an *H. capsulatum* M antigen-specific fragment of nucleic acid which is 90% similar to a nucleic acid consisting of a nucleotide sequence as set forth in the Sequence Listing as SEQ ID NO:1; or
    an *H. capsulatum* M antigen-specific fragment of a nucleic acid consisting of a nucleotide sequence which is 90% similar to a nucleic acid which is complementary to the nucleotide sequence set forth in the Sequence Listing as SEQ ID NO:1;
    wherein the nucleic acid does not contain the nucleotide sequences 5'CGAAGTCGAGGCTTTCAGCATG3' (SEQ ID NO:14), 5'TATTAGCTCTAGAATTAC- CACGGGTATCCAAGTAGTAAGG3' (SEQ ID NO:15), 5'CCCCGAAGGGCATTGGTTTTT- TATCTAATAAATACACCCC3' (SEQ ID NO:16), or nucleotide sequences complementary thereto,
    and wherein the nucleic acid is not a nucleic acid consisting essentially of between 10 and 100 nucleotides which is able to form a hybrid at 60° C. with a nucleotide polymer consisting of a nucleotide sequence of 5'CGAAGTCGAGGCTTTCAGCATG3' (SEQ ID NO:17), 5'CATGCTGAAAGCCTCGACTTCG3' (SEQ ID NO:18), 5'CAUGCUGAAAGCCUCGACU- UCG3' (SEQ ID NO:19) or 5'CGAAGUCGAGGCU- UUCAGCAUG3' (SEQ ID NO:20).

12. An isolated nucleic acid consisting of:
    a nucleic acid consisting of a nucleotide sequence as set forth in the Sequence Listing as SEQ ID NO:1;
    a nucleic acid consisting of a nucleotide sequence which is complementary to the nucleotide sequence set forth in the Sequence Listing as SEQ ID NO:1;
    an *H. capsulatum* M antigen-specific nucleic acid which is 95% similar to a nucleic acid consisting of a nucleotide sequence as set forth in the Sequence Listing as SEQ ID NO:1;
    an *H. capsulatum* M antigen-specific nucleic acid which is 95% similar to a nucleic acid consisting of a nucleotide sequence which is complementary to the nucleotide sequence set forth in the Sequence Listing as SEQ ID NO:1;

an *H. capsulatum* M antigen-specific fragment of a nucleic acid consisting of a nucleotide sequence as set forth in the Sequence Listing as SEQ ID NO:1;

an *H. capsulatum* M antigen-specific fragment of a nucleic acid consisting of a nucleotide sequence which is complementary to the nucleotide sequence set forth in the Sequence Listing as SEQ ID NO:1;

an *H. capsulatum* M antigen-specific fragment of nucleic acid which is 95% similar to a nucleic acid consisting of a nucleotide sequence as set forth in the Sequence Listing as SEQ ID NO:1; or an *H. capsulatum* M antigen-specific fragment of a nucleic acid consisting of a nucleotide sequence which is 95% similar to a nucleic acid which is complementary to the nucleotide sequence set forth in the Sequence Listing as SEQ ID NO:1;

wherein the nucleic acid does not contain the nucleotide sequences 5'CGAAGTCGAGGCTTTCAGCATG3' (SEQ ID NO:14), 5'TATTAGCTCTAGAATTAC-CACGGGTATCCAAGTAGTAAGG3'(SEQ ID NO:15), 5'CCCCGAAGGGCATTGGTTTTT-TATCTAATAAATACACCCC3' (SEQ ID NO:16), or nucleotide sequences complementary thereto, and wherein the nucleic acid is not a nucleic acid consisting essentially of between 10 and 100 nucleotides which is able to form a hybrid at 60° C. with a nucleotide polymer consisting of a nucleotide sequence of 5'CGAAGTCGAGGCTTTCAGCATG3' (SEQ ID NO:17), 5'CATGCTGAAAGCCTCGACTTCG3' (SEQ ID NO:18), 5'CAUGCUGAAAGCCUCGACU-UCG3' (SEQ ID NO:19) or 5'CGAAGUCGAGGCU-UUCAGCAUG3' (SEQ ID NO:20).

13. An isolated *Histoplasma capsulatum* M antigen-specific nucleic acid comprising:

a nucleic acid having a nucleotide sequence as set forth in the Sequence Listing as SEQ ID NO:1; or a nucleic acid having a nucleotide sequence which is complementary to the nucleotide sequence set forth in the Sequence Listing as SEQ ID NO:1;

wherein the nucleic acid does not contain the nucleotide sequences 5'CGAAGTCGAGGCTTTCAGCATG3' (SEQ ID NO:14), 5'TATTAGCTCTAGAATTAC-CACGGGTATCCAAGTAGTAAGG3' (SEQ ID NO:15), 5'CCCCGAAGGGCATTGGTTTTT-TATCTAATAAATACACCCC3' (SEQ ID NO:16), or nucleotide sequences complementary thereto, and wherein the nucleic acid is not a nucleic acid consisting essentially of between 10 and 100 nucleotides which is able to form a hybrid at 60° C. with a nucleotide polymer consisting of a nucleotide sequence of 5'CGAAGTCGAGGCTTTCAGCATG3' (SEQ ID NO:17), 5'CATGCTGAAAGCCTCGACTTCG3' (SEQ ID NO:18), 5'CAUGCUGAAAGCCUCGACU-UCG3' (SEQ ID NO:19) or 5'CGAAGUCGAGGCU-UUCAGCAUG3' (SEQ ID NO:20).

14. An isolated nucleic acid consisting of:

an *H. capsulatum* M antigen-specific fragment of a nucleic acid of SEQ ID NO:1; or an *H. capsulatum* M antigen-specific fragment of a nucleic acid of a nucleotide sequence which is complementary to the nucleotide sequence set forth in the Sequence Listing as SEQ ID NO:1;

wherein the nucleic acid does not contain the nucleotide sequences 5'CGAAGTCGAGGCTTTCAGCATG3' (SEQ ID NO:14), 5'TATTAGCTCTAGAATTAC-CACGGGTATCCAAGTAGTAAGG3' (SEQ ID NO:15), 5'CCCCGAAGGGCATTGGTTTTT-TATCTAATAAATACACCCC3' (SEQ ID NO:16), or nucleotide sequences complementary thereto, and wherein the nucleic acid is not a nucleic acid consisting essentially of between 10 and 100 nucleotides which is able to form a hybrid at 60° C. with a nucleotide polymer consisting of a nucleotide sequence of 5'CGAAGTCGAGGCTTTCAGCATG3' (SEQ ID NO:17), 5'CATGCTGAAAGCCTCGACTTCG3' (SEQ ID NO:18), 5'CAUGCUGAAAGCCUCGACU-UCG3' (SEQ ID NO:19) or 5'CGAAGUCGAGGCU-UUCAGCAUG3' (SEQ ID NO:20).

15. An isolated *Histoplasma capsulatum* M antigen-specific nucleic acid selected from the group consisting of:

a nucleic acid having a nucleotide sequence as set forth in the Sequence Listing as SEQ ID NO:1;

a nucleic acid having a nucleotide sequence which is complementary to the nucleotide sequence set forth in the Sequence Listing as SEQ ID NO:1;

an *H. capsulatum* M antigen-specific fragment of a nucleic acid, the nucleic acid consisting of a nucleotide sequence as set forth in the Sequence Listing as SEQ ID NO:1; and an *H. capsulatum* M antigen-specific fragment of a nucleic acid, the nucleic acid consisting of a nucleotide sequence which is complementary to the nucleotide sequence set forth in the Sequence Listing as SEQ ID NO:1;

wherein the nucleic acid does not contain the nucleotide sequences 5'CGAAGTCGAGGCTTTCAGCATG3' (SEQ ID NO:14), 5'TATTAGCTCTAGAATTAC-CACGGGTATCCAAGTAGTAAGG3' (SEQ ID NO:15), 5'CCCCGAAGGGCATTGGTTTTT-TATCTAATAAATACACCCC3' (SEQ ID NO:16), or nucleotide sequences complementary thereto, and wherein the nucleic acid is not a nucleic acid consisting essentially of between 10 and 100 nucleotides which is able to form a hybrid at 60° C. with a nucleotide polymer consisting of a nucleotide sequence of 5'CGAAGTCGAGGCTTTCAGCATG3' (SEQ ID NO:17), 5'CATGCTGAAAGCCTCGACTTCG3' (SEQ ID NO:18), 5'CAUGCUGAAAGCCUCGACU-UCG3' (SEQ ID NO:19) or 5'CGAAGUCGAGGCU-UUCAGCAUG3' (SEQ ID NO:20).

* * * * *

UNITED STATES PATENT AND TRADEMARK OFFICE
CERTIFICATE OF CORRECTION

PATENT NO.         : 7,018,827 B1  
APPLICATION NO. : 09/674195  
DATED                 : March 28, 2006  
INVENTOR(S)        : Zancopé-Oliveira et al.

Page 1 of 1

It is certified that error appears in the above-identified patent and that said Letters Patent is hereby corrected as shown below:

On front page of patent, first column, section (54), line 5 of title, word reading "Histoplasmas" should read --Histoplasmosis--  
      Column 1, line 5 of title, word reading "Histoplasmas" should read --Histoplasmosis--

Signed and Sealed this

Twelfth Day of September, 2006

JON W. DUDAS  
*Director of the United States Patent and Trademark Office*